(12) United States Patent
Ostrovsky et al.

(10) Patent No.: US 10,582,923 B2
(45) Date of Patent: *Mar. 10, 2020

(54) APPARATUS FOR DELIVERING AND ANCHORING IMPLANTABLE MEDICAL DEVICES

(71) Applicant: Boston Scientific Scimed, Inc., Maple Grove, MN (US)

(72) Inventors: Isaac Ostrovsky, Wellesley, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 499 days.

This patent is subject to a terminal disclaimer.

(21) Appl. No.: 14/610,861

(22) Filed: Jan. 30, 2015

(65) Prior Publication Data

US 2015/0148820 A1   May 28, 2015

Related U.S. Application Data

(63) Continuation of application No. 12/760,049, filed on Apr. 14, 2010, now Pat. No. 8,968,334.
(Continued)

(51) Int. Cl.
*A61B 17/04* (2006.01)
*A61B 17/06* (2006.01)
(Continued)

(52) U.S. Cl.
CPC ...... *A61B 17/0469* (2013.01); *A61B 17/0401* (2013.01); *A61B 17/06109* (2013.01);
(Continued)

(58) Field of Classification Search
CPC ............ A61B 17/0401; A61B 17/0461; A61B 17/0462; A61B 17/0469;
(Continued)

(56) References Cited

U.S. PATENT DOCUMENTS 527,263 A   10/1894   Blanchard
3,182,662 A   5/1965   Shirodkar
(Continued)

FOREIGN PATENT DOCUMENTS

DE   3223153 C1   8/1983
DE   4220283 A1   12/1993
(Continued)

OTHER PUBLICATIONS

International Search Report and Written Opinion for PCT Application No. PCT/US2009/040587, dated Oct. 21, 2009, 13 pages.
(Continued)

*Primary Examiner* — David C Eastwood
(74) *Attorney, Agent, or Firm* — Brake Hughes Bellermann LLP

(57) ABSTRACT

An apparatus includes an elongate member having a distal end portion and a proximal end portion. The elongate member defines a longitudinal axis. The distal end portion of the elongate member defines a notch having a face defining an axis. The axis of the face and the longitudinal axis define an acute angle with respect to a first direction along the longitudinal axis. The notch is configured to retain a loop of a suture when the elongate member is moved through a tissue of a patient in the first direction along the longitudinal axis. The notch is configured to release the loop of the suture when the elongate member is moved through the tissue of the patient in a second direction different than the first direction. The suture has at least one tissue anchor configured to be disposed within the tissue of the patient.

14 Claims, 10 Drawing Sheets

Related U.S. Application Data

(60) Provisional application No. 61/170,312, filed on Apr. 17, 2009.

(51) Int. Cl.
  *A61B 17/00* (2006.01)
  *A61B 90/00* (2016.01)

(52) U.S. Cl.
  CPC .............. *A61B 2017/00805* (2013.01); *A61B 2017/0462* (2013.01); *A61B 2017/06042* (2013.01); *A61B 2090/036* (2016.02)

(58) Field of Classification Search
  CPC .... A61B 2017/0409; A61B 2017/0411; A61B 2017/0412; A61B 2017/0414; A61B 2017/0464; A61B 2017/06109; A61B 2017/06042
  USPC ....... 606/139, 144, 232, 172, 148, 185–189, 606/222–227; 604/117, 178, 179, 180, 604/181, 198
  See application file for complete search history.

(56) References Cited

U.S. PATENT DOCUMENTS

| | | |
|---|---|---|
| 3,212,502 A | 10/1965 | Myers |
| 3,311,110 A | 3/1967 | Singerman et al. |
| 3,372,695 A | 3/1968 | Beliveau et al. |
| 3,472,232 A | 10/1969 | Earl |
| 3,565,073 A | 2/1971 | Giesy |
| 3,608,095 A | 9/1971 | Barry |
| 3,704,712 A | 12/1972 | Giesy et al. |
| 3,763,860 A | 10/1973 | Clarke |
| 3,858,783 A | 1/1975 | Kapitanov et al. |
| 3,924,633 A | 12/1975 | Cook et al. |
| 4,037,603 A | 7/1977 | Wendroff |
| 4,128,100 A | 12/1978 | Wendroff |
| 4,221,212 A | 9/1980 | Miller |
| 4,235,238 A | 11/1980 | Ogiu et al. |
| 4,392,495 A | 7/1983 | Bayers |
| 4,441,497 A | 4/1984 | Paudler |
| 4,509,516 A | 4/1985 | Richmond |
| 4,549,545 A | 10/1985 | Levy |
| 4,583,540 A | 4/1986 | Malmin |
| 4,735,615 A | 4/1988 | Uddo, Jr. et al. |
| 4,798,193 A | 1/1989 | Giesy et al. |
| 4,824,435 A | 4/1989 | Giesy et al. |
| 4,872,451 A | 10/1989 | Moore et al. |
| 4,946,467 A | 8/1990 | Ohi et al. |
| 4,946,468 A | 8/1990 | Li |
| 4,976,717 A | 12/1990 | Boyle |
| 5,002,550 A | 3/1991 | Li |
| 5,013,292 A | 5/1991 | Lemay |
| 5,032,508 A | 7/1991 | Naughton et al. |
| 5,064,435 A | 11/1991 | Porter |
| 5,078,730 A | 1/1992 | Li et al. |
| 5,080,667 A | 1/1992 | Chen et al. |
| 5,084,058 A | 1/1992 | Li |
| 5,085,661 A | 2/1992 | Moss |
| 5,087,263 A | 2/1992 | Li |
| 5,112,344 A | 5/1992 | Petros |
| 5,149,329 A | 9/1992 | Richardson |
| 5,152,749 A | 10/1992 | Giesy et al. |
| 5,180,385 A | 1/1993 | Sontag |
| 5,207,679 A | 5/1993 | Li |
| 5,217,438 A | 6/1993 | Richard et al. |
| 5,250,033 A | 10/1993 | Evans et al. |
| 5,256,150 A | 10/1993 | Quiachon et al. |
| 5,281,237 A | 1/1994 | Gimpelson |
| 5,292,327 A | 3/1994 | Dodd et al. |
| 5,312,422 A | 5/1994 | Trott |
| 5,334,185 A | 8/1994 | Giesy et al. |
| 5,337,736 A | 8/1994 | Reddy |
| 5,362,294 A | 11/1994 | Seitzinger |
| 5,368,595 A | 11/1994 | Lewis |
| 5,368,756 A | 11/1994 | Vogel et al. |
| 5,382,257 A | 1/1995 | Lewis et al. |
| 5,383,904 A | 1/1995 | Totakura et al. |
| 5,395,349 A | 3/1995 | Quiachon et al. |
| 5,403,328 A | 4/1995 | Shallman |
| 5,439,467 A | 8/1995 | Benderev et al. |
| 5,441,508 A | 8/1995 | Gazielly et al. |
| 5,450,860 A | 9/1995 | O'Connor |
| 5,456,722 A | 10/1995 | McLeod et al. |
| 5,499,991 A | 3/1996 | Garman et al. |
| 5,505,735 A | 4/1996 | Li |
| 5,507,796 A | 4/1996 | Hasson |
| 5,520,700 A | 5/1996 | Beyar et al. |
| 5,527,342 A | 6/1996 | Pietrzak et al. |
| 5,540,703 A | 6/1996 | Barker et al. |
| 5,571,119 A | 11/1996 | Atala |
| 5,582,188 A | 12/1996 | Benderev et al. |
| 5,611,515 A | 3/1997 | Benderev et al. |
| 5,628,756 A | 5/1997 | Barker et al. |
| 5,645,568 A | 7/1997 | Chervitz et al. |
| 5,645,589 A | 7/1997 | Li |
| 5,683,418 A | 11/1997 | Luscombe et al. |
| 5,690,649 A | 11/1997 | Li |
| 5,702,215 A | 12/1997 | Li |
| 5,741,299 A | 4/1998 | Rudt |
| 5,742,943 A | 4/1998 | Chen |
| 5,749,884 A | 5/1998 | Benderev et al. |
| 5,816,258 A | 10/1998 | Jervis |
| 5,836,315 A | 11/1998 | Benderev et al. |
| 5,840,011 A | 11/1998 | Landgrebe et al. |
| 5,855,549 A | 1/1999 | Newman |
| 5,860,425 A | 1/1999 | Benderev et al. |
| 5,860,993 A | 1/1999 | Thompson et al. |
| 5,891,168 A | 4/1999 | Thal |
| 5,899,906 A | 5/1999 | Schenk |
| 5,899,909 A | 5/1999 | Claren et al. |
| 5,899,999 A | 5/1999 | De Bonet |
| 5,931,855 A | 8/1999 | Buncke |
| 5,934,283 A | 8/1999 | Willem et al. |
| 5,935,122 A | 8/1999 | Fourkas et al. |
| 5,945,122 A | 8/1999 | Abra et al. |
| 5,954,057 A | 9/1999 | Li |
| 5,984,933 A | 11/1999 | Yoon |
| 5,997,554 A | 12/1999 | Thompson |
| 6,010,447 A | 1/2000 | Kardjian |
| 6,030,393 A | 2/2000 | Corlew |
| 6,039,686 A | 3/2000 | Kovac |
| 6,042,534 A | 3/2000 | Gellman et al. |
| 6,050,937 A | 4/2000 | Benderev |
| 6,053,935 A | 4/2000 | Brenneman et al. |
| 6,096,041 A | 8/2000 | Gellman et al. |
| 6,099,547 A | 8/2000 | Gellman et al. |
| 6,110,101 A | 8/2000 | Tihon et al. |
| 6,117,067 A | 9/2000 | Gil-Vernet |
| 6,200,330 B1 * | 3/2001 | Benderev ........... A61B 17/0401 411/358 |
| 6,221,005 B1 | 4/2001 | Bruckner et al. |
| 6,221,084 B1 | 4/2001 | Fleenor |
| 6,264,676 B1 | 7/2001 | Gellman et al. |
| 6,273,852 B1 | 8/2001 | Lehe et al. |
| 6,306,079 B1 | 10/2001 | Trabucco |
| 6,306,156 B1 | 10/2001 | Clark |
| 6,334,446 B1 | 1/2002 | Beyar |
| 6,382,214 B1 | 5/2002 | Raz et al. |
| 6,398,787 B1 | 6/2002 | Itoman |
| 6,406,423 B1 | 6/2002 | Scetbon |
| 6,423,072 B1 | 7/2002 | Zappala |
| 6,423,080 B1 | 7/2002 | Gellman et al. |
| 6,475,139 B1 | 11/2002 | Miller |
| 6,478,727 B2 | 11/2002 | Scetbon |
| 6,491,703 B1 | 12/2002 | Ulmsten |
| 6,494,887 B1 | 12/2002 | Kaladelfos |
| 6,530,943 B1 | 3/2003 | Hoepffner et al. |
| 6,582,443 B2 | 6/2003 | Cabak et al. |
| 6,596,001 B2 | 7/2003 | Stormby et al. |
| 6,596,002 B2 | 7/2003 | Therin et al. |
| 6,599,235 B2 | 7/2003 | Kovac |
| 6,605,097 B1 | 8/2003 | Lehe et al. |

(56) References Cited

U.S. PATENT DOCUMENTS

| | | | |
|---|---|---|---|
| 6,612,977 B2 | 9/2003 | Staskin et al. | |
| 6,635,058 B2 * | 10/2003 | Beyar | A61B 17/0401 606/232 |
| 6,638,209 B2 | 10/2003 | Landgrebe | |
| 6,638,210 B2 | 10/2003 | Berger | |
| 6,638,211 B2 | 10/2003 | Suslian et al. | |
| 6,641,525 B2 | 11/2003 | Rocheleau et al. | |
| 6,648,921 B2 | 11/2003 | Anderson et al. | |
| 6,652,450 B2 | 11/2003 | Neisz et al. | |
| 6,652,561 B1 | 11/2003 | Tran | |
| 6,685,629 B2 | 2/2004 | Therin | |
| 6,691,711 B2 | 2/2004 | Raz et al. | |
| 6,730,110 B1 | 5/2004 | Harari et al. | |
| 6,755,781 B2 | 6/2004 | Gellman | |
| 6,802,807 B2 | 10/2004 | Anderson et al. | |
| 6,830,052 B2 | 12/2004 | Carter et al. | |
| 6,848,152 B2 | 2/2005 | Genova | |
| 6,932,759 B2 | 8/2005 | Kammerer et al. | |
| 7,377,926 B2 | 5/2008 | Topper et al. | |
| 7,381,212 B2 | 6/2008 | Topper et al. | |
| 7,387,634 B2 | 6/2008 | Benderev | |
| 7,524,281 B2 | 4/2009 | Chu et al. | |
| 8,449,573 B2 | 5/2013 | Chu | |
| 8,591,545 B2 | 11/2013 | Lunn et al. | |
| 8,968,334 B2 * | 3/2015 | Ostrovsky | A61B 17/0401 606/139 |
| 9,011,489 B2 | 4/2015 | Ostrovsky et al. | |
| 9,289,204 B2 | 3/2016 | Chu | |
| 2001/0018549 A1 | 8/2001 | Scetbon | |
| 2001/0037119 A1 | 11/2001 | Schmieding | |
| 2001/0049467 A1 | 12/2001 | Lehe et al. | |
| 2002/0028980 A1 | 3/2002 | Thierfelder et al. | |
| 2002/0058959 A1 | 5/2002 | Gellman | |
| 2002/0072694 A1 | 6/2002 | Snitkin et al. | |
| 2002/0077526 A1 | 6/2002 | Kammerer et al. | |
| 2002/0091373 A1 | 7/2002 | Berger | |
| 2002/0116025 A1 | 8/2002 | Haab | |
| 2002/0128670 A1 | 9/2002 | Ulmsten et al. | |
| 2002/0138025 A1 | 9/2002 | Gellman et al. | |
| 2002/0147382 A1 | 10/2002 | Neisz et al. | |
| 2002/0151910 A1 | 10/2002 | Gellman et al. | |
| 2002/0161382 A1 | 10/2002 | Neisz et al. | |
| 2002/0188169 A1 | 12/2002 | Kammerer et al. | |
| 2002/0188301 A1 | 12/2002 | Dallara et al. | |
| 2003/0004395 A1 | 1/2003 | Therin | |
| 2003/0004580 A1 | 1/2003 | Sump et al. | |
| 2003/0009181 A1 | 1/2003 | Gellman et al. | |
| 2003/0010929 A1 | 1/2003 | Priewe et al. | |
| 2003/0023135 A1 | 1/2003 | Ulmsten et al. | |
| 2003/0023138 A1 | 1/2003 | Luscombe | |
| 2003/0028075 A1 | 2/2003 | Ulmsten et al. | |
| 2003/0050530 A1 | 3/2003 | Neisz et al. | |
| 2003/0065336 A1 | 4/2003 | Xiao | |
| 2003/0088272 A1 | 5/2003 | Smith | |
| 2003/0100954 A1 | 5/2003 | Schuldt-Hempe et al. | |
| 2003/0120309 A1 * | 6/2003 | Colleran | A61B 17/0401 606/232 |
| 2003/0130670 A1 | 7/2003 | Anderson et al. | |
| 2003/0149440 A1 | 8/2003 | Kammerer et al. | |
| 2003/0171644 A1 | 9/2003 | Anderson et al. | |
| 2003/0171778 A1 | 9/2003 | Lizardi | |
| 2003/0176762 A1 | 9/2003 | Kammerer | |
| 2003/0195386 A1 | 10/2003 | Thierfelder et al. | |
| 2003/0220538 A1 | 11/2003 | Jacquetin | |
| 2004/0002734 A1 * | 1/2004 | Fallin | A61B 17/0401 606/232 |
| 2004/0039453 A1 | 2/2004 | Anderson et al. | |
| 2004/0087978 A1 | 5/2004 | Velez et al. | |
| 2004/0098053 A1 | 5/2004 | Tran | |
| 2004/0106847 A1 | 6/2004 | Benderev | |
| 2004/0237736 A1 | 12/2004 | Genova et al. | |
| 2005/0203576 A1 | 9/2005 | Sulamanidze et al. | |
| 2005/0228406 A1 | 10/2005 | Bose | |
| 2006/0173491 A1 | 8/2006 | Meade et al. | |
| 2006/0217589 A1 | 9/2006 | Wan et al. | |
| 2006/0229596 A1 | 10/2006 | Weiser et al. | |
| 2006/0282161 A1 | 12/2006 | Huynh et al. | |
| 2007/0016135 A1 * | 1/2007 | Kanner | A61M 5/46 604/117 |
| 2007/0038249 A1 | 2/2007 | Kolster | |
| 2007/0112384 A1 * | 5/2007 | Conlon | A61B 17/0401 606/232 |
| 2007/0129758 A1 | 6/2007 | Saadat | |
| 2008/0103527 A1 | 5/2008 | Martin et al. | |
| 2008/0132931 A1 | 6/2008 | Mueller | |
| 2009/0076529 A1 * | 3/2009 | Ganti | A61M 25/00 606/151 |
| 2009/0287245 A1 | 11/2009 | Ostrovsky et al. | |
| 2010/0268255 A1 | 10/2010 | Ostrovsky et al. | |
| 2010/0324357 A1 | 12/2010 | Chu | |
| 2011/0106108 A1 | 5/2011 | Ostrovsky et al. | |
| 2013/0253259 A1 | 9/2013 | Chu | |
| 2016/0193025 A1 | 7/2016 | Chu | |

FOREIGN PATENT DOCUMENTS

| | | |
|---|---|---|
| DE | 4334419 A1 | 4/1995 |
| DE | 10103179 A1 | 7/2001 |
| DE | 2007015955 U1 | 4/2009 |
| EP | 0598976 A2 | 6/1994 |
| EP | 0599772 A1 | 6/1994 |
| EP | 0688056 A1 | 12/1995 |
| EP | 0774240 A1 | 5/1997 |
| EP | 0941712 A1 | 9/1999 |
| EP | 1025811 A2 | 8/2000 |
| FR | 2422386 A1 | 11/1979 |
| JP | 2005-532848 A | 11/2005 |
| JP | 2006-515204 A | 5/2006 |
| JP | 2007-532174 A1 | 11/2007 |
| JP | 2007-535335 A | 12/2007 |
| RU | 1225547 A1 | 4/1986 |
| RU | 1443873 A1 | 12/1988 |
| SE | 503271 C2 | 4/1996 |
| WO | 1990/003766 A1 | 4/1990 |
| WO | 1996/006567 A1 | 3/1996 |
| WO | 1996/006597 A1 | 3/1996 |
| WO | 1997/013465 A1 | 4/1997 |
| WO | 1998/031301 A1 | 7/1998 |
| WO | 1998/034545 A1 | 8/1998 |
| WO | 2000/074594 A1 | 12/2000 |
| WO | 2001/006951 A1 | 2/2001 |
| WO | 2001/078609 A2 | 10/2001 |
| WO | 2002/026108 A2 | 4/2002 |
| WO | 2002/028312 A1 | 4/2002 |
| WO | 2002/038079 A2 | 5/2002 |
| WO | 2004/012626 A1 | 2/2004 |
| WO | 2004/112585 A2 | 12/2004 |
| WO | 2005/122954 A1 | 12/2005 |
| WO | 2006/108145 A1 | 10/2006 |
| WO | 2007/098212 A2 | 8/2007 |
| WO | 2008/020937 A2 | 2/2008 |
| WO | 2008/087635 A2 | 7/2008 |
| WO | 2009/140012 A1 | 11/2009 |
| WO | 2010/065274 A1 | 6/2010 |
| WO | 2010/121052 A2 | 10/2010 |
| WO | 2010/121052 A3 | 1/2011 |

OTHER PUBLICATIONS

International Search Report and written Opinion for PCT Application No. PCT/US2009/064564, dated Feb. 23, 2010, 13 pages.

International Preliminary Report on Patentability for PCT Patent Application No. PCT/US2009/040587, dated Nov. 25, 2010, 10 pages.

International Search Report and Written opinion for PCT Patent Application No. PCT/US2010/031273, dated Dec. 1, 2010, 17 Pages.

International Preliminary Report on Patentability for PCT Application No. PCT/US2009/064564, dated Jun. 16, 2011, 9 pages.

Restriction Requirement for U.S. Appl. No. 12/760,049, dated Mar. 29, 2012, 9 pages.

(56) References Cited

OTHER PUBLICATIONS

Response to Restriction Requirement for U.S. Appl. No. 12/760,049, filed Apr. 27, 2012, 2 pages.
Non-Final Office Action for U.S. Appl. No. 12/760,049, dated Jun. 1, 2012, 10 pages.
Response to Non-Final Office Action for U.S. Appl. No. 12/760,049, filed Aug. 29, 2012, 8 pages.
Final Office Action for U.S. Appl. No. 12/760,049, dated Nov. 8, 2012, 17 pages.
Response to Final Office Action for U.S. Appl. No. 12/760,049, filed Feb. 8, 2013, 8 pages.
Non-Final Office Action for U.S. Appl. No. 12/760,049, dated Oct. 3, 2013, 18 pages.
Response to Non-Final Office Action for U.S. Appl. No. 12/760,049, filed Dec. 23, 2013, 10 pages.
Final Office Action for U.S. Appl. No. 12/760,049, dated Apr. 4, 2014, 37 pages.
Response to Final Office Action for U.S. Appl. No. 12/760,049, filed May 28, 2014, 9 pages.
Non-Final Office Action for U.S. Appl. No. 12/760,049, dated Jun. 19, 2014, 22 pages.
Response to Non-Final Office Action for U.S. Appl. No. 12/760,049, filed Sep. 17, 2014, 9 pages.
Notice of Allowance for U.S. Appl. No. 12/760,049, dated Oct. 24, 2014, 7 pages.
Restriction Requirement for U.S. Appl. No. 12/394,965, dated May 18, 2011, 6 pages.
Restriction Requirement Response for U.S. Appl. No. 12/394,965, filed Jun. 15, 2011, 1 page.
Non-Final Office Action for U.S. Appl. No. 12/394,965, dated Aug. 8, 2011, 8 pages.
Response to Non-Final Office Action for U.S. Appl. No. 12/394,965, filed Nov. 3, 2011, 10 pages.
Non-Final Office Action for U.S. Appl. No. 12/394,965, dated Mar. 2, 2012, 13 pages.
Response to Non-Final Office Action for U.S. Appl. No. 12/394,965, filed Jun. 4, 2012, 09 pages.
Final Office Action for U.S. Appl. No. 12/394,965, dated Dec. 7, 2012, 15 pages.
Response to Final Office Action for U.S. Appl. No. 12/394,965, filed Mar. 5, 2013, 9 pages.
Non-Final Office Action for U.S. Appl. No. 12/394,965, dated Mar. 21, 2013, 14 pages.
Response to Non-Final Office Action for U.S. Appl. No. 12/394,965, filed Jul. 17, 2013, 10 pages.
Final Office Action for U.S. Appl. No. 12/394,965, dated Oct. 31, 2013, 13 pages.
Response to Final Office Action for U.S. Appl. No. 12/394,965, filed Jan. 31, 2014, 11 pages.
Notice of Allowance for U.S. Appl. No. 12/394,965, dated Dec. 17, 2014, 8 pages.
Non-Final Office Action for U.S. Appl. No. 12/549,704, dated Sep. 26, 2011, 9 pages.
Response to Non-Final Office Action for U.S. Appl. No. 12/549,704, filed Dec. 23, 2011, 7 pages.
Final Office Action for U.S. Appl. No. 12/549,704, dated Jan. 30, 2012, 10 pages.
Response to Final Office Action for U.S. Appl. No. 12/549,704, filed Apr. 27, 2012, 8 pages.
Non-Final Office Action for U.S. Appl. No. 12/549,704, dated Jul. 25, 2012, 10 pages.
Response to Non-Final Office Action for U.S. Appl. No. 12/549,704, filed Oct. 25, 2012, 8 pages.
Final Office Action for U.S. Appl. No. 12/549,704, dated Nov. 20, 2012, 12 pages.
Response to Final Office Action for U.S. Appl. No. 12/549,704, filed Jan. 18, 2013, 8 pages.
Notice of Allowance for U.S. Appl. No. 12/549,704, dated Feb. 1, 2013, 9 pages.

Restriction Requirement for U.S. Appl. No. 12/938,553, dated Dec. 28, 2012, 9 pages.
Response to Restriction Requirement for U.S. Appl. No. 12/938,553, filed Jan. 25, 2013, 2 pages.
Non-Final Office Action for U.S. Appl. No. 12/938,553, dated Jun. 7, 2013, 7 pages.
Response to Non-Final Office Action for U.S. Appl. No. 12/938,553, filed Sep. 3, 2013, 8 pages.
Non-Final Office Action for U.S. Appl. No. 12/938,553, dated Dec. 19, 2013, 8 pages.
Response to Non-Final Office Action for U.S. Appl. No. 12/938,553, filed Mar. 17, 2014, 8 pages.
Final Office Action for U.S. Appl. No. 12/938,553, dated Aug. 6, 2014, 8 pages.
Response to Final Office Action for U.S. Appl. No. 12/938,553, filed Sep. 30, 2014, 7 pages.
Advisory Action for U.S. Appl. No. 12/938,553, dated Oct. 21, 2014, 2 pages.
Office Action for Japanese Patent Application No. 2011-509522, dated May 22, 2013, 4 pages. (Official Communication Only).
Office Action for Japanese Patent Application No. 2011-509522, dated Sep. 13, 2013, 2 pages. (Official Communication Only).
Office Action for Japanese Patent Application No. 2011-509522, dated Jun. 12, 2014, 7 pages. (3 Pages Office Action + 4 Pages English translation).
First Examiner Report for Australian Patent Application No. 2009322835, dated May 21, 2014, 3 pages.
Bayer et al., "A New Approach to Primary Strengthening of Colostomy With Marlex Mesh to Prevent Paracolostomy Hernia", Surg Gynecol Obstet, vol. 163, No. 6 ,Dec. 1986 ,1 page. (Abstract Only).
Delorme, Emmanuel, "La Bandelette Trans-Obturatrice: Un Procede Mini-Invasif Pour Traiter L'incontinence Urinaire D'effort De La Femme", Progres en Urologie with English translated Abstract ,2001 ,pp. 1306-1313 and 1 page of translation.
Fianu et al., "Absorbable Polyglactin Mesh for Retropubic Sling Operation in Female Urinary Stress Incontinence", Gynecol. Obstet. Invest., vol. 16, 1983, pp. 45-50 , 1983 , 1 page.
Giberti, C. , "TVT Tension-free Vaginal Tape, Minimally Invasive Highly Effective Treatment for Female Stress Unrinary Incontinence", Urology vol. 57 No. 4 ,2001 ,pp. 666-669.
Gittes et al., "No-Incision Pubovaginal Suspension for Stress Incontinence", Journal of Urology, vol. 138 No. 3 , Sep. 1987 , pp. 568-570.(Abstract Only).
Haab et al., "Feasibility of Outpatient Percutaneous Bladder Neck Suspension Under Local Anesthesia", Urology vol. 50 No. 4 ,Oct. 1997 ,pp. 585-587.(Abstract Only).
Kovac et al., "Pubic Bone Suburethral Stabilization Sling for Recurrent Urinary Incontinence", Obstetrics & Gynecology, vol. 89, No. 4, Apr. 1997, pp. 624-627.(Abstract Only).
Norris et al., "Use of Synthetic Material in Sling Surgery: A Minimally Invasive Approach", Journal of Endourology, vol. 10, Issue 3 ,Jun. 1996 ,pp. 227-230.(Abstract Only).
Petros et al., "An Integral Theory and Its Method for the Diagnosis and Management of Female Urinary Incontinence", Scandinavian Journal of Urology and Nephrology, An Integral Theory and its Method for the Diagnosis ,1993, pp. 1-93.
Petros, P., "An Integral Theory of Bladder Neck Opening, Closure and Urinary incontinence in the Female", International Journal of Gynecology & Obstetrics. XXIII World Congress of Gynaecology and Obstetrics (FIGO) ,1991.
Petro, P. P., "Medium-term Follow-up of the Intravaginal Slingplasty Operation Indicates Minimal Deterioration of Urinary Continence with Time", Aust NZ J Obstet Gynaecol vol. 39 No. 3 ,Aug. 1999,pp. 354-356.
Petros, P., "The Intravaginal Slingplasty Operation, a Minimally Invasive Technique for Cure of Urinary Incontinence in the Female", Aust. NZ J Obstet Gynaecol, vol. 36, No. 4 ,1996, pp. 453-461. (Abstract Only).
Petros et al., "Urethral Pressure Increase on Effort Originates from Within the Urethra, and Continence From Musculovaginal Closure", Neurourology and Urodynamics vol. 14 No. 4 ,1995 ,pp. 337-346.

(56) References Cited

OTHER PUBLICATIONS

Petros, P E., "Vault Prolapse I: Dynamic Supports of the Vagina", Int Urogynecol J Pelvic Floor Dysfunct vol. 12 No. 5, 2001, pp. 292-295.

Raz et al., "Fascial Sling to Correct Male Neurogenic Sphincter Incompetence: The McGuire/RAZ Approach", Journal of Urology vol. 139 No. 3, Mar. 1988, pp. 528-531.

Raz, S., "Modified Bladder Neck Suspension for Female Stress Incontinence", Urology vol. 17 No. 1, Jan. 1981, pp. 82-85.

Raz et al., "Vaginal Wall Sling", The Journal of Urology vol. 141, 1989, pp. 43-46.

Richardson, P A., "Ambulatory Surgery for Urinary Incontinence and Vaginal Prolapse", Medical Journal of Australia vol. 161 No. 8, 1994, pp. 171-172.

Stamey, Thomas A., "Endoscopic Suspension of the Vesical Neck for Urinary Incontinence in Females", Annals of Surgery vol. 192 No. 4, Oct. 1980, pp. 465-471.

Starney, T. A., "Endoscopic Suspension of the Vesical Neck for Urinary Incontinence Surgery", Gynecology & Obstetrics vol. 136 No. 4, 1973, pp. 547-554.

Staskin, D. R., "Sling Surgery for the Treatment of Female", Stress Incontinence vol. 5 No. 1, 1991, pp. 106-122.

Staskin et al., "The Gore-Tex Sling Procedure for Female Sphincteric Incontinence: Indications, Technique, and Results", World J of Urol. vol. 15 No. 5, 1997, pp. 295-299.

Ulmsten, U., "An Ambulatory Surgical Procedure Under Local Anesthesia for Treatment of Female Urinary Incontinence", The International Urogynecology Journal vol. 7 No. 2, 1996, pp. 81-86.

Ulmsten, U., "An Introduction to Tension-Free Vaginal Tape (TVT)—A New Surgical Procedure for Treatment of Female Urinary Incontinence", Int Urogynecol J. Pelvic Floor Dysfunct. (Suppl 2), 2001, pp. S3-S4.

Ulmsten, U., "Connective Tissue Factors in the Aetiology of Female Pelvic Disorders", Ann. Med vol. 22 No. 6, Dec. 1990, pp. 403.

Ulmsten et al., "Intravaginal Slingplasty", Zentralbl Gynakol vol. 116, 1994, pp. 398-404.

Ulmsten et al., "Intravaginal Slingplasty (IVS): An Ambulatory Surgical Procedure for Treatment of Female Urinary Incontinence", Scand J Urol Nephrol vol. 29 No. 1, Mar. 1995, pp. 75-82.

Ulmsten et al., "Surgery for Female Urinary Incontinence", Current Opinion in Obstetrics & Gynecology vol. 4 No. 3, 1992, pp. 456-462.

Ulmsten, U., "The Basic Understanding and Clinical Results of Tension-Free Vaginal Tape for Stress Urinary Incontinence", Urologe A., Jul. 2001, pp. 269-273.

freedictionary.com, "Suture", available online at <http://www.thefreedictionary.com/suture>, Retrieved on May 21, 2012, 3 pages.

\* cited by examiner

APPARATUS FOR DELIVERING AND ANCHORING IMPLANTABLE MEDICAL DEVICES

CROSS REFERENCE TO RELATED APPLICATIONS

This application is a Continuation of, and claims priority to, U.S. patent application Ser. No. 12/760,049, filed on Apr. 14, 2010, entitled "APPARATUS FOR DELIVERING AND ANCHORING IMPLANTABLE MEDICAL DEVICES", which, in turn, claims the benefit of and priority to U.S. Patent Application No. 61/170,312, filed on Apr. 17, 2009, entitled "APPARATUS FOR AND METHOD OF DELIVERING AND ANCHORING IMPLANTABLE MEDICAL DEVICES", both of which are incorporated by reference herein their entireties.

BACKGROUND

This invention relates to a medical device and more particularly to methods and devices for delivering a suture including tissue anchors.

Sutures including tissue anchors have application to a wide variety of surgical procedures including those that require high anchoring strength. For example, one such procedure is directed to female urinary incontinence and involves insertion of a suture to be fixed to bodily tissue under and/or lateral to the urethra to reconstitute the ligamentary support for the urethra. Generally, the suture is inserted into two or more body tissues to couple the body tissues tightly together without knotting the suture.

In other procedures a suture having tissue anchors is coupled to an implant that is configured to support a portion of a body of a patient. In such a procedure, the tissue anchor must be able to support the implant without tearing through the tissue within which it is disposed.

Tissue anchors that are large or have many barbs are often difficult to insert into a tissue. When inserting such tissue anchors, a large incision is often necessary and bulky delivery tools are often used. Using a large incision or bulky delivery tools causes unwanted trauma to the tissue and can weaken the tissue within which the tissue anchor is disposed. Thus, a need exists for devices and methods that can be used to effectively deliver a suture having tissue anchors to a tissue of a patient.

SUMMARY

An apparatus includes an elongate member having a distal end portion and a proximal end portion. The elongate member defines a longitudinal axis. The distal end portion of the elongate member defines a notch having a face defining an axis. The axis of the face and the longitudinal axis define an acute angle with respect to a first direction along the longitudinal axis. The notch is configured to retain a loop of a suture when the elongate member is moved through a tissue of a patient in the first direction along the longitudinal axis. The notch is configured to release the loop of the suture when the elongate member is moved through the tissue of the patient in a second direction different than the first direction. The suture has at least one tissue anchor configured to be disposed within the tissue of the patient.

DETAILED DESCRIPTION

Figure 1:
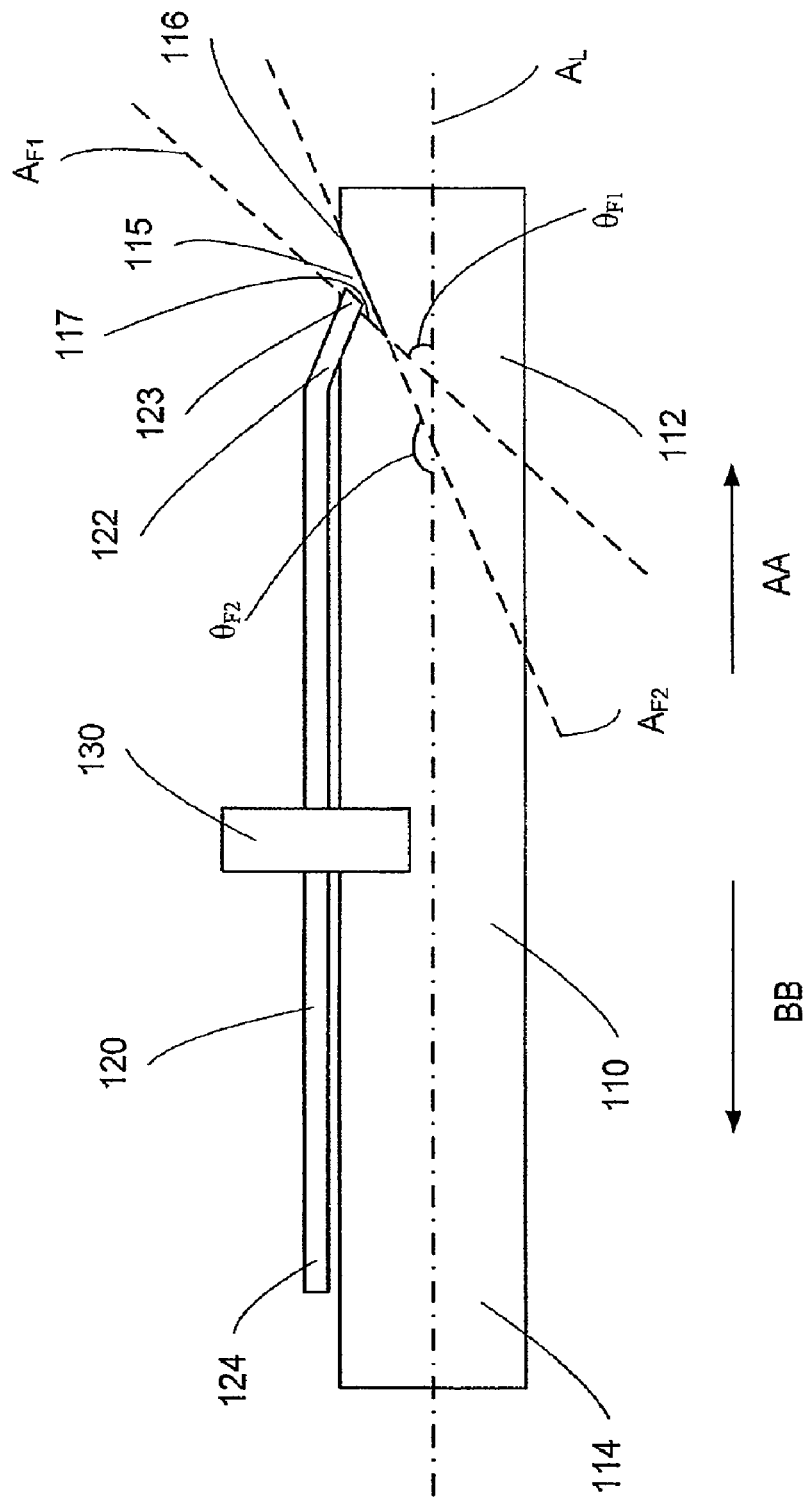
FIG. 1 is a schematic illustration of a suture attached to a delivery device, according to an embodiment.

In some embodiments, an apparatus includes an elongate member having a distal end portion and a proximal end portion. The elongate member defines a longitudinal axis. The distal end portion of the elongate member defines a notch having a face defining an axis. The axis of the face and the longitudinal axis define an acute angle with respect to a first direction along the longitudinal axis. The notch is configured to retain a loop of a suture when the elongate member is moved through a tissue of a patient in the first direction along the longitudinal axis. The notch is configured to release the loop of the suture when the elongate member is moved through the tissue of the patient in a second direction different than the first direction. The suture has at least one tissue anchor configured to be disposed within the tissue of the patient.

In some embodiments, an apparatus includes an elongate member and an adjustable stop. The elongate member has a distal end portion and a proximal end portion. The distal end portion of the elongate member defines a notch configured to releasably retain a loop of a suture when the elongate member is inserted into a tissue of a patient a distance. The adjustable stop is movably coupled to the elongate member. The adjustable stop is configured to allow a user to determine the distance the elongate member is inserted into the tissue.

In some embodiments, an apparatus includes an elongate member having a distal end portion and a proximal end portion. The elongate member defines a longitudinal axis and an outer perimeter. The distal end portion of the elongate member has a tissue piercing tip and an oblique shoulder facing toward the tissue piercing tip. The oblique shoulder is disposed proximal to the tissue piercing tip along the longitudinal axis and is within the outer perimeter defined by the elongate member.

In some embodiments, a medical device includes an elongate member, a suture and an anchor. The elongate member has a distal end portion and a proximal end portion. The distal end portion of the elongate member defines a notch. The suture has a distal end portion and a proximal end portion. The distal end portion of the suture has a loop configured to be inserted into the notch. The notch is configured to retain the loop of the suture when the elongate member is inserted into a tissue of a patient. The anchor is coupled to the suture and configured to retain the suture within the tissue of the patient when the suture is disposed within the tissue of the patient and the elongate member is removed from the tissue of the patient.

In some embodiments, a method of inserting a suture within a body of a patient includes sliding an adjustable stop along an elongate member. A loop of a suture is attached to a distal end portion of the elongate member. A tissue anchor is coupled to the suture. The tissue anchor is inserted into a tissue of a patient by moving the elongate member through the tissue of the patient until the adjustable stop contacts an outer surface of the tissue of the patient. The distal end portion of the elongate member is disposed within the tissue a distance from the outer surface of the tissue. The distance from the outer surface of the tissue is substantially equal to a distance between the distal end portion of the elongate member and the adjustable stop. The loop of the suture is the released from the distal end portion of the elongate member and the elongate member is removed from the body of the patient.

As used herein, the terms proximal portion or proximal end refer to the portion or end, respectively, of a device that is closest to a medical practitioner (e.g., a physician) when performing a medical procedure, and the terms distal portion or distal end refer to the portion or end, respectively, of the device that is furthest from the physician during a medical procedure. For example, the end of a medical device first inserted inside the patient's body would be the distal end of the medical device, while the end of the medical device handled by the medical practitioner would be the proximal end of the medical device.

FIG. 1 is a schematic illustration of a suture 120 attached to a delivery device 110, according to an embodiment. The suture 120 includes a proximal end portion 124, a distal end portion 122 and a tissue anchor 130. The suture 120 can be made of any biocompatible material. For example, the suture 120 can be a monofilament suture, a braided suture, a tape, a mesh, include a mesh-like material and/or any other material known in the art. In some embodiments, the suture is similar to the sutures shown and described in U.S. Provisional Patent Application No. 61/071,726 entitled "Surgical Composite Barbed Suture," filed on May 14, 2008, which is hereby incorporated by reference in its entirety.

The proximal end portion 124 of the suture 120 is configured to be attached to any device configured to be retained within a body of a patient, such as an implant (not shown in FIG. 1). Such an implant can be configured to be placed within a body of a patient and can be configured to support a portion of the body. For example, the implant can be similar to the implants or grafts disclosed in U.S. Patent Application No. 61/017,257 entitled "Apparatus and Method for Uterine Preservation," filed on Dec. 28, 2007, which is hereby incorporated by reference in its entirety. The implant can be a variety of different shapes, sizes and configurations depending on the intended use for the particular implant. In some embodiments, the implant can be substantially rectangular, square, oval, or elliptical. The implant can be shaped and sized to support a bladder and/or a bladder neck (e.g., to treat a cystocele), a uterus (e.g., to treat a hysterocele) and/or a rectum (e.g. to treat a rectocele).

The implant can be formed with a mesh material to allow tissue in-growth to the implant after implantation. For example, some or all of the implant can be formed with a mesh material as described in U.S. Patent Pub. 2005/0038452 A1 to Chu, the disclosure of which is hereby incorporated by reference in its entirety. In some embodiments, some or all of the implant can be formed with the Advantage® Mesh or the Polyform™ Synthetic Mesh material each provided by Boston Scientific Corporation.

The distal end portion 122 of the suture 120 includes an attachment portion 123 configured to be releasably attached to the delivery device 110, described in further detail herein. In some embodiments, the attachment portion 123 of the distal end portion 122 of the suture 120 can be, for example, a loop configured to be inserted into a notch 115 of the delivery device 110. In other embodiments, the attachment portion can be a clip, an adhesive portion, and/or any other attachment mechanism known in the art.

The tissue anchor 130 can be any device configured to retain the suture 120 within a tissue of a patient. In some embodiments, for example, the tissue anchor 130 is similar to the tissue anchors shown and described in U.S. Provisional Patent Application No. 61/071,726 entitled "Surgical Composite Barbed Suture," filed on May 14, 2008, which is hereby incorporated by reference in its entirety.

The tissue anchor 130 is configured to retain its position with respect to bodily tissue when inserted into bodily tissue. In some embodiments, the tissue anchor 130 includes a retaining member, for example, a barb, a prong, a tab, and/or any other retaining member known in the art. In other embodiments, the tissue anchor includes multiple retaining members extending from the elongate member. In some embodiments, the retaining members can flex or bend to facilitate insertion into bodily tissue. In other embodiments, the retaining members are rigid and are not configured to bend or flex during insertion.

The tissue anchor 130 is constructed of any suitable material. In some embodiments, for example, the tissue anchor 130 is constructed of a biocompatible polymer, a metal, and/or any other material known in the art. In some embodiments, the tissue anchor 130 includes an opaque material to increase the visibility of the medical practitioner during insertion of the suture 120.

The tissue anchor 130 is coupled to the suture 120 by any suitable means. In some embodiments, for example, the tissue anchor 130 is coupled to the suture 120 via a knot, an adhesive, such as, for example, glue, and/or any other attachment mechanism known in the art. In other embodiments, the tissue anchor is monolithically formed with the suture and/or molded to the suture. In some embodiments, the tissue anchor 130 is coupled near the distal end portion 122 of the suture 120. In such embodiments, the distal end portion 112 of the delivery device 110 need not be inserted as far into the body of the patient for the tissue anchor 130 to be disposed within the tissue of the patient. This decreases the trauma caused to the tissue of the patient beyond the portion of the tissue where the tissue anchor 130 is disposed.

The delivery device 110 includes a distal end portion 112 and a proximal end portion 114 and defines a longitudinal axis $A_L$. The delivery device 110 is configured to be moved through a tissue of a patient in a direction substantially parallel to the longitudinal axis $A_L$. In some embodiments, the delivery device 110 is substantially rigid and/or solid. In other embodiments, the delivery device defines a lumen. The proximal end portion 114 of the delivery device 110 is controlled by the medical practitioner directly by holding the proximal end portion 114 or indirectly by controlling another device coupled to the proximal end portion 114 when the distal end portion 112 of the delivery device 110 is inserted into the tissue of the patient.

The distal end portion 112 of the delivery device 110 defines a notch 115 or a shoulder configured to releasably retain the attachment portion 123 of the distal end portion 122 of the suture 120. The notch 115 includes a first face 117 and a second face 116. The first face 117 defines an axis $A_{F1}$. In other embodiments, the notch only includes a first face. In some embodiments, the notch 115 or shoulder is within an outer parameter defined by the delivery device 110. In other embodiments, the notch or shoulder extends outside the outer parameter defined by the delivery device.

The axis $A_{F1}$ of the first face 117 defines an angle $S_{F1}$ with the longitudinal axis AL. The angle $S_{F1}$ defined by the axis $A_{F1}$ of the first face 117 and the longitudinal axis AL is acute with respect to a first direction shown by the arrow AA in FIGS. 1 and 2. The angle $S_{F1}$ is configured to retain the attachment portion 123 of the suture 120 when the delivery device 110 is moved in the first direction AA, as described in further detail herein.

Similarly, the second face 116 defines an axis $A_{F2}$. The axis $A_{F2}$ of the second face 116 defines an angle $0_{F2}$ with the longitudinal axis AL. The angle $0_{F2}$ defined by the axis $A_{F2}$ of the second face 116 and the longitudinal axis $A_L$ is obtuse with respect to a second direction shown by the arrow BB in FIGS. 1 and 3. The angle $0_{F2}$ is configured to allow the attachment portion 123 of the suture 120 to become uncoupled from the notch 115 of the delivery device 110 when the delivery device 110 is moved in the second direction BB, as described in further detail herein.

The distal end portion 112 of the delivery device 110 is configured to be inserted into the body of the patient to assist in delivering the suture 120 within a tissue of the patient. In some embodiments, the distal end portion includes a tapered portion configured to pierce and/or dilate tissue as the delivery device is inserted into the tissue of the patient.

In use, the suture 120 is attached to the delivery device 110 by attaching the attachment portion 123 of the distal end portion 122 of the suture 120 to the notch 115 defined by the delivery device 110. In some embodiments, this includes inserting a loop of the suture 120 into the notch 115 of the delivery device 110. The proximal end portion 124 of the suture 120 is aligned substantially parallel to the longitudinal axis AL defined by the delivery device 110. Said another way, a longitudinal axis defined by the suture is aligned such that it is substantially parallel to the longitudinal axis AL defined by the delivery device 110. Positioning the suture 120 along the longitudinal axis AL allows the suture 120 to be inserted into the tissue of the patient through a lumen created by the delivery device 110 as the delivery device 110 moves through the tissue of the patient.

Figure 2:
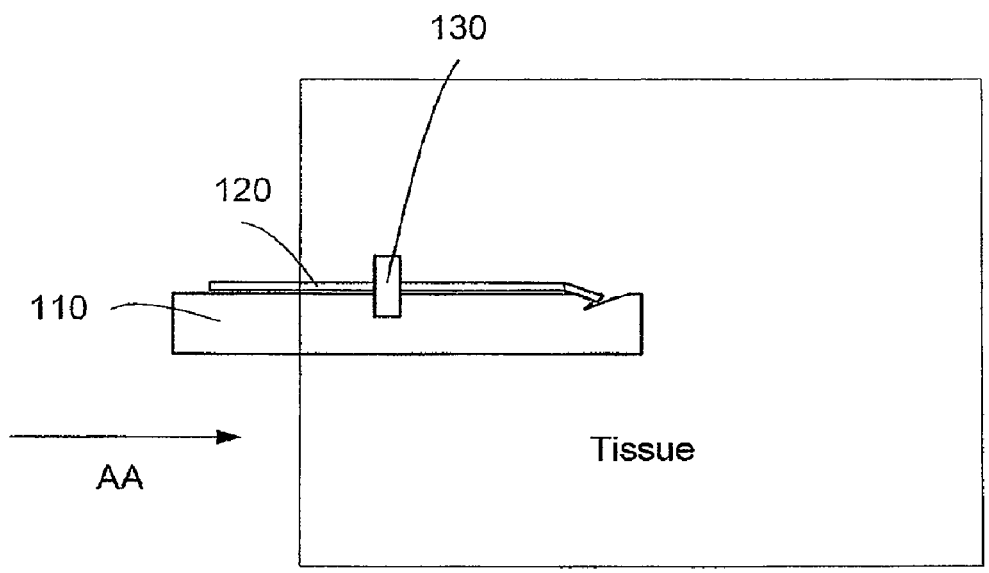
FIGS. 2 and 3 are schematic illustrations of the delivery device of FIG. 1 inserting the suture of FIG. 1 into a tissue of a patient.
Figure 3:
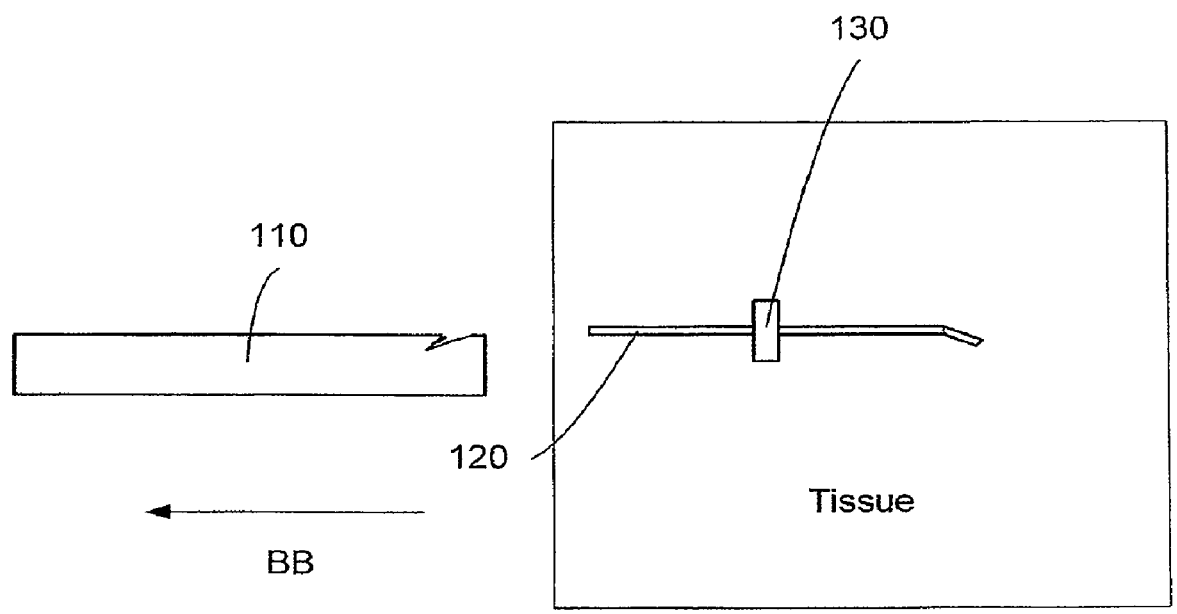

FIGS. 2 and 3 are schematic illustrations of the delivery device 110 inserting the suture 120 into a tissue of a patient. The delivery device 110 and the suture 120 are inserted into the tissue of the patient by moving the delivery device 110 with respect to the tissue in a first direction along the longitudinal axis AL shown by the arrow AA in FIG. 2. The first face 117 of the notch 115 exerts a force on the attachment portion 123 of the suture 120 that is normal to the first face 117 of the notch 115 as the delivery device 110 is moved in the first direction AA. Because the angle $S_{F1}$ defined by the axis $A_{F1}$ of the first face 117 of the notch 115 is acute with respect to the first direction AA, the force exerted on the attachment portion 123 of the suture 120 by the first face 117 of the notch 115 retains the attachment portion 123 of the suture 120 in the notch 115 as the delivery device 110 is moved in the first direction AA.

Once the tissue anchor 130 reaches a depth within the tissue where it is to be disposed, the medical practitioner can release the attachment portion 123 of the suture 120 from the notch 115 of the delivery device 110 by moving the delivery device 110 in a second direction along the longitudinal axis AL shown by the arrow BB in FIG. 3. The second direction BB is substantially opposite the first direction AA. Because the angle $S_{F2}$ defined by the axis $A_{F2}$ of the second face 116 of the notch 115 and the longitudinal axis AL is obtuse with respect to the second direction BB, the attachment portion 123 of the suture 120 is released from the notch 115 as the delivery device 110 is moved in the second direction BB.

Said another way, when the delivery device 110 is moved in the second direction BB, the second face 116 of the notch 115 exerts a force on the attachment portion 123 of the suture 120 that is normal to the second face 116. This force pushes the attachment portion 123 of the suture 120 out of the notch 115. Once the attachment portion 123 of the suture 120 is released from the notch 115, the medical practitioner can remove the delivery device 110 from the tissue of the patient by continuing to move the delivery device 110 in the second direction BB.

Figure 4:
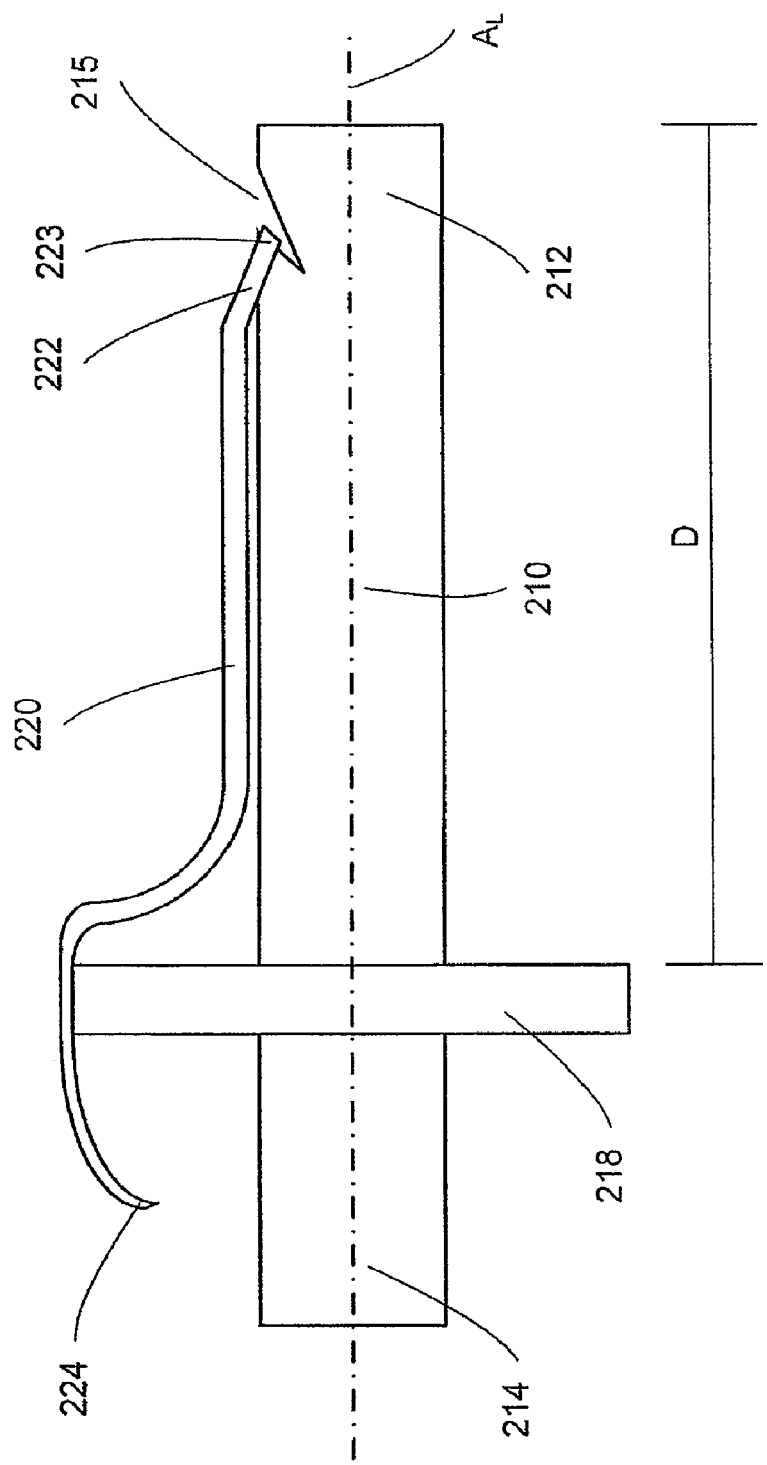
FIG. 4 is a schematic illustration of a suture attached to a delivery device, according to an embodiment.

FIG. 4 is a schematic illustration of a suture 220 attached to a delivery device 210, according to another embodiment. The suture 220 includes a proximal end portion 224, and a distal end portion 222. The proximal end portion 224 of the suture 220 is configured to be attached to any device configured to be retained within a body of a patient, such as an implant (not shown in FIG. 4).

The distal end portion 222 of the suture 220 includes an attachment portion 223 configured to be releasably attached to the delivery device 210. In some embodiments, the attachment portion 223 of the distal end portion 222 of the suture 220 can be, for example, a loop configured to be inserted into a notch 215 of the delivery device 210. In other embodiments, the attachment portion 223 can be a clip, an adhesive portion, and/or any other attachment mechanism known in the art.

In some embodiments, the suture 220 includes a tissue anchor (not shown in FIG. 4) and/or another device configured to assist in retaining the suture within the tissue of the patient. In other embodiments, the suture does not include a tissue anchor. In such embodiments, the friction between the tissue surrounding the suture and the suture can help retain the suture within the tissue.

The delivery device 210 includes a distal end portion 212 and a proximal end portion 214 and defines a longitudinal axis AL. The delivery device 210 is configured to be moved through a tissue of a patient in a direction substantially parallel to the longitudinal axis AL. In some embodiments, the delivery device 210 is substantially rigid and/or solid. In other embodiments, the delivery device defines a lumen. The proximal end portion 214 of the delivery device 210 is controlled by the medical practitioner directly by holding the proximal end portion 214 or indirectly by controlling another device coupled to the proximal end portion 214 when the distal end portion 212 of the delivery device 210 is inserted into the tissue of the patient.

The distal end portion 212 of the delivery device 210 defines a notch 215 or a shoulder configured to releasably retain the attachment portion 223 of the distal end portion 222 of the suture 220. The distal end portion 212 of the delivery device 210 is configured to be inserted into the body of the patient to assist in delivering the suture 220 within a tissue of the patient. In some embodiments, the distal end portion includes a tapered portion configured to pierce and/or dilate tissue as the delivery device is inserted into the tissue of the patient.

An adjustable stop 218 is movably coupled to the delivery device 210. The adjustable stop 218 is configured to be disposed in at least two positions with respect to the delivery device 210. In some embodiments, for example, the adjustable stop 218 has a first configuration and a second configuration. When the adjustable stop 218 is in its first configuration, the location of the adjustable stop 218 with respect to the delivery device 210 is fixed. Said another way, when the adjustable stop 218 is in its first configuration it cannot slide with respect to the delivery device 210. Accordingly, when the adjustable stop 218 is in its first configuration, the distance D shown in FIG. 4 does not change and the adjustable stop's 218 position with respect to the delivery device 210 is fixed. When the adjustable stop 218 is in its second configuration it is configured to slide with respect to the delivery device 210 in a direction substantially along the longitudinal axis AL.

In other embodiments, the adjustable stop does not slide with respect to the delivery device but instead is coupled to the delivery device in a desired location with respect to the delivery device. In such embodiments, in order to move the adjustable stop with respect to the delivery device the adjustable stop is uncoupled from the delivery device and recoupled to the delivery device in another location.

The adjustable stop 218 is configured to help limit the distance that the distal end portion 212 of the delivery device 210 can be inserted into the tissue of the patient. The distance that the distal end portion 212 of the delivery device 210 can be inserted into the patient is substantially equal to the distance between the distal end portion 212 of the delivery device 210 and the adjustable stop 218 shown as distance D in FIG. 4. Having an adjustable stop 218 prevents a medical practitioner from inserting the distal end portion 212 of the delivery device 210 into the tissue of the patient further than expected, causing unwanted harm to the patient. The adjustable stop 218 also provides the medical practitioner with the ability to determine a depth within the tissue of the patient where the distal end portion 224 of the suture 220 is to be disposed, and, using the adjustable stop 218, set the delivery device 210 to deliver the distal end portion 224 of the suture 220 to this depth, as further described in detail herein.

In use, the medical practitioner moves the adjustable stop 218, in its second configuration, with respect to the delivery device 210 to adjust the distance D between the distal end portion 212 of the delivery device 210 and the adjustable stop 218. As discussed above, the distance D corresponds to the depth the distal end portion 212 of the delivery device can be inserted into the tissue of the patient. Once the adjustable stop 218 is in the position along the delivery device 210 that corresponds to the desired depth, the adjustable stop 218 is moved from its second configuration to its first configuration. As discussed above, when the adjustable stop 218 is in its first configuration, the location of the adjustable stop 218 with respect to the delivery device 210 is fixed. Accordingly, the desired depth cannot be inadvertently changed prior to and/or during the insertion process.

The suture 220 is attached to the delivery device 210 by attaching the attachment portion 223 of the distal end portion 222 of the suture 220 to the notch 215 defined by the delivery device 210. In some embodiments, this includes inserting a loop of the suture 220 into the notch 215 of the delivery device 210. The proximal end portion 224 of the suture 220 is aligned substantially parallel to the longitudinal axis AL defined by the delivery device 210. Once the adjustable stop 218 has been adjusted and moved to its first configuration and the suture 220 has been attached to the delivery device 210, the suture 220 can be inserted into the tissue of the patient similar to suture 120.

Figure 5:
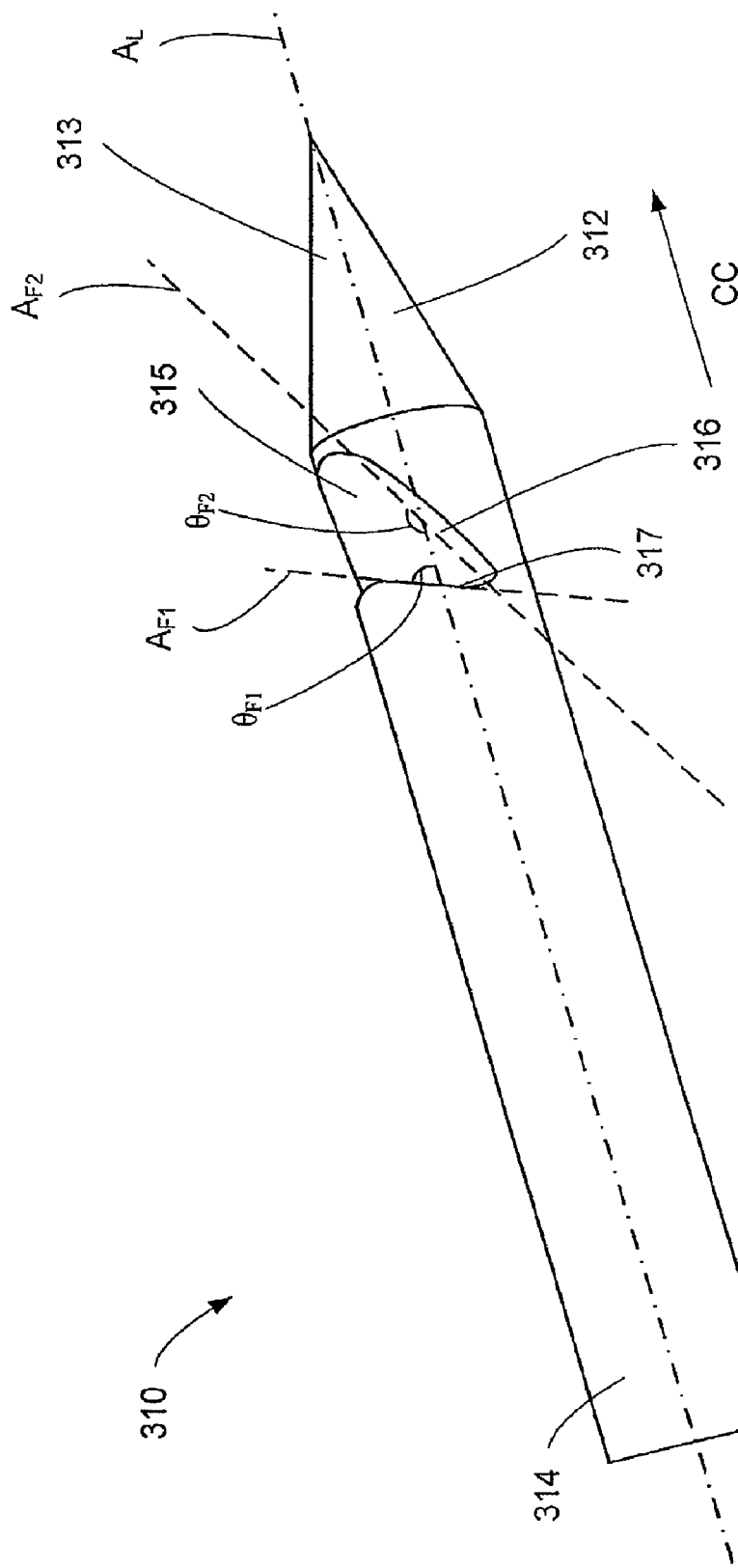
FIG. 5 is a perspective view of a delivery device, according to an embodiment.

FIG. 5 is a perspective view of a delivery device 310 configured to deliver a suture within a tissue of a patient, according to another embodiment. The delivery device 310 includes a distal end portion 312 and a proximal end portion 314 and defines a longitudinal axis $A_L$. The delivery device 310 is configured to be moved through the tissue of the patient in a direction substantially parallel to the longitudinal axis AL. In some embodiments, the delivery device 310 is substantially rigid and/or solid. In other embodiments, the delivery device defines a lumen. The proximal end portion 314 of the delivery device 310 is controlled by the medical practitioner directly by holding the proximal end portion 314 or indirectly by controlling another device coupled to the proximal end portion 314 when the distal end portion 312 of the delivery device 310 is inserted into the tissue of the patient.

The proximal end portion 314 of the delivery device 310 is configured to be held by a medical practitioner and/or indirectly controlled by a medical practitioner when the distal end portion 312 of the delivery device is inserted into the tissue of the patient.

The distal end portion 312 of the delivery device 310 includes a tapered portion 313 and defines a notch 315 or a shoulder. The distal end portion 312 of the delivery device 310 is configured to be inserted into the tissue of the patient to assist in delivering a suture within the tissue of the patient. The tapered portion 313 of the distal end portion 312 has a sharp tip configured to pierce the tissue and is tapered. This allows the tapered portion 313 to dilate tissue as the delivery device 310 is inserted into the tissue of the patient. Accordingly, the tapered portion 313 pierces and dilates a tissue in which a suture will be disposed.

The notch 315 defined by the distal end portion 312 of the delivery device 310 is configured to releasably retain an attachment portion of a suture. The attachment portion of the suture can be, for example, a loop on the distal end portion of the suture and/or any other attachment mechanism known in the art. The notch 315 includes a first face 317 and a second face 316. In other embodiments, the notch includes only a first face. In some embodiments, the notch 315 or shoulder is within an outer parameter defined by the delivery device 310. In other embodiments, the notch or shoulder extends outside the outer parameter defined by the delivery device.

The first face 317 defines an axis $A_{F1}$. The axis $A_{F1}$ of the first face 317 defines an angle 8F1 with the longitudinal axis AL. The angle 8F1 defined by the axis $A_{F1}$ of the first face 317 and the longitudinal axis AL is acute with respect to a first direction shown by the arrow CC in FIG. 5. The angle 8F1 is configured to retain the attachment portion of the suture 320 when the delivery device 310 is moved in the first direction CC, as described in further detail herein.

Similarly, the second face 316 defines an axis $A_{F2}$. The axis $A_{F2}$ of the second face 316 defines an angle $O_{F2}$ with the longitudinal axis $A_L$. The angle $O_{F2}$ defined by the axis $A_{F2}$ of the second face 316 and the longitudinal axis AL is obtuse with respect to a second direction shown by the arrow DD in FIG. 5. The angle $O_{F2}$ is configured to allow the attachment portion of the suture to become uncoupled from the notch 315 of the delivery device 310 when the delivery device 310 is moved in the second direction DD, as described in further detail herein.

Figure 7:
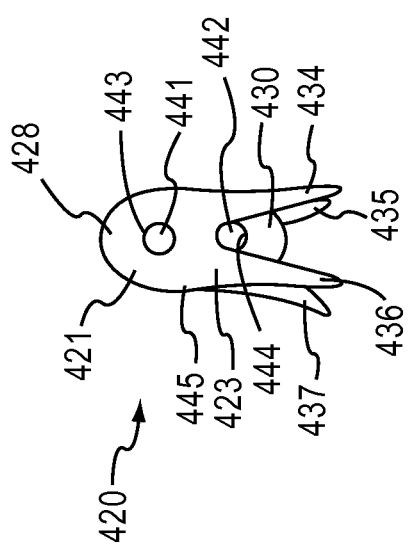
FIG. 7 is a side view of a tissue anchor shown in FIG. 6.
Figure 6:
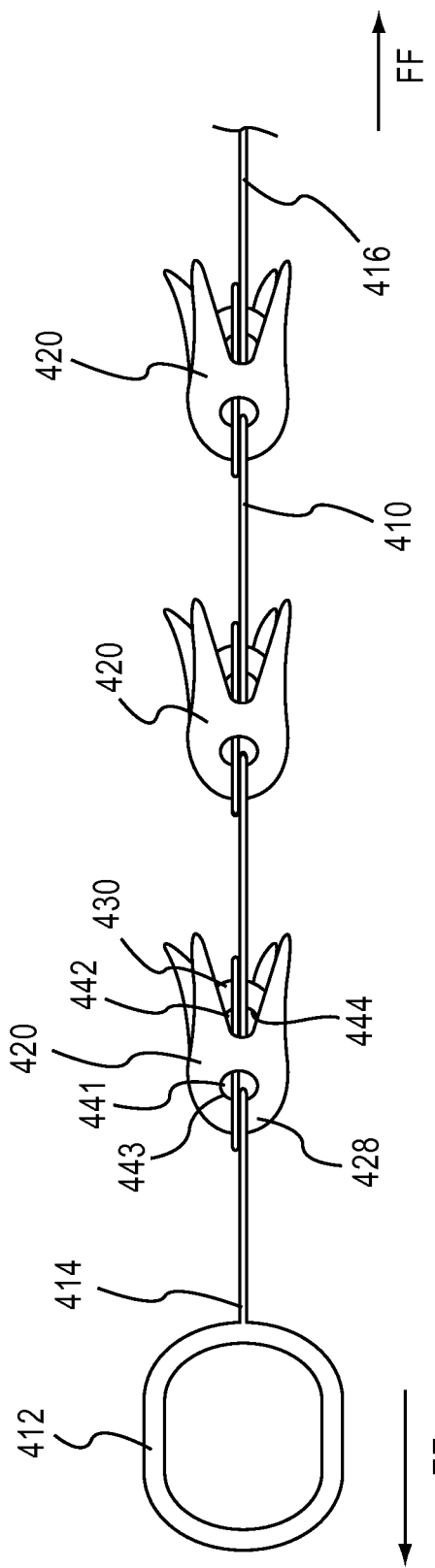
FIG. 6 is a side view of multiple tissue anchors coupled to a suture, according to an embodiment.

FIGS. 6 and 7 show a side view of multiple tissue anchors 420 coupled to a suture 410 and a perspective view of a tissue anchor 420, respectively, according to another embodiment. The suture 410 includes a distal end portion 414 and a proximal end portion 416. The suture 410 can be made of any biocompatible material. For example, the suture 410 can be a monofilament suture, a braided suture, a tape, a mesh, include a mesh-like material and/or any other material known in the art.

The distal end portion 414 of the suture 410 includes a loop 412. The loop 410 is configured to be releasably coupled to a delivery device, as described in further detail herein. In some embodiments, for example, the loop 412 is configured to be releasably coupled to a notch of a delivery device such as the notch 315 of delivery device 310. In other embodiments, the suture can include other attachment mechanisms, such as, for example, a clip, an adhesive portion, and/or any other attachment mechanism known in the art.

The tissue anchor 420 has a first end portion 421 and a second end portion 423 opposite the first end portion 421. As shown in FIG. 6, the first end portion 421 of the tissue anchor 420 includes a coupling portion 428 coupled to the suture 410. The second end portion 423 of the tissue anchor 420 includes a coupling portion 430 coupled to the suture 410. Specifically, the tissue anchor 420 has a first side portion 445 and a second side portion (not shown) opposite the first side portion 445. The tissue anchor 420 defines a first opening 441 that extends from the first side portion 445 to the second side portion. The coupling portion 428 of the first end portion 421 includes the inner wall 443 of the first opening 441 such that when the suture 410 is coupled to the first end portion 421, the suture 410 engages the inner wall 443 of the first opening 441 of the first end portion 421 as shown in FIG. 6. Similarly, the tissue anchor 420 defines a second opening 442 that extends from the first side portion 445 to the second side portion. The coupling portion 430 of the second end portion 423 includes an inner wall 444 of the second opening 442 of the second end portion 423 such that when the suture 410 is coupled to the second end portion 423 the suture 410 engages the inner wall 444 of the second opening 442 of the second end portion 423 as shown in FIG. 6.

As shown in FIG. 6, the suture 410 is coupled to the first end portion 421 and the second end portion 423. Specifically, a portion of the inner wall 443 of the first opening 441 is disposed within a first knot formed by the suture 410. Similarly, a portion of the inner wall 444 of the second opening 442 is disposed within a second knot formed by the suture 410. In some embodiments, the suture 410 can form more or less than two knots. In other embodiments, the tissue anchor can be coupled to the suture in any suitable manner. For example, the tissue anchor can be coupled to the suture via the methods shown and described in U.S. Provisional Patent Application No. 61/071,726 entitled "Surgical Composite Barbed Suture," filed on May 14, 2008, which is hereby incorporated by reference in its entirety.

The tissue anchor 420 includes multiple retaining members 434, 435, 436, 437. The retaining members 434, 435, 436, 437 are configured to allow movement of the suture 410 with respect to the tissue through the tissue of the patient in a first direction shown by the arrow EE in FIG. 6. This allows the suture 410 to pass through the tissue of the patient when being inserted into the tissue of the patient, as further described herein. The retaining members 434, 435, 436, 437 help limit the movement of the suture 410 with respect to the tissue in a second direction, substantially opposite the first direction shown by the arrow FF in FIG. 6. Accordingly, once the suture 410 is placed within the tissue of the patient the anchors 420 help prevent the suture 410 from inadvertently becoming dislodged from the tissue.

Figure 8:
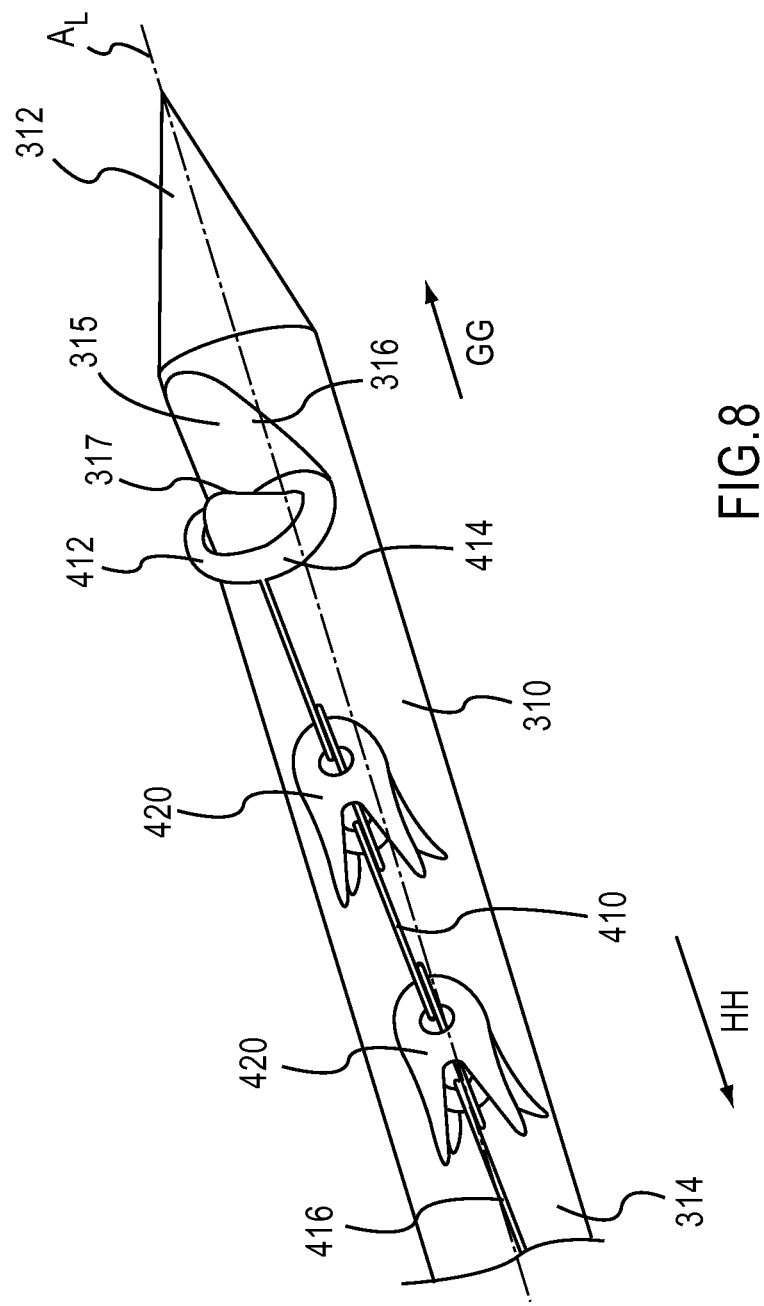
FIG. 8 is a perspective view of the suture of FIG. 6 attached to the delivery device of FIG. 5.

FIG. 8 is a side perspective view of the suture 410 shown in FIG. 6 attached to the delivery device 310 shown in FIG. 5. The suture 410 is attached to the delivery device 310 by attaching the loop 412 of the suture 410 to the notch 315 defined by the delivery device 310. The proximal end portion 416 of the suture 410 is aligned substantially parallel to the longitudinal axis AL defined by the delivery device 310. Said another way, a longitudinal axis defined by the suture is aligned such that it is substantially parallel to the longitudinal axis AL defined by the delivery device 310. Positioning the suture 410 along the longitudinal axis AL allows the suture 410 to be inserted into the tissue of the patient through a lumen created by the delivery device 310 as the delivery device 310 moves through the tissue of the patient.

The delivery device 310 and the suture 410 are inserted into the tissue of the patient by moving the delivery device 310 with respect to the tissue in a first direction along the longitudinal axis AL shown by the arrow GG in FIG. 8. The first face 317 of the notch 315 exerts a force on the loop 412 of the suture 410 that is normal to the first face 317 of the notch 315 as the delivery device 310 is moved in the first direction GG. Because the angle $\theta_{F1}$ defined by the axis $A_{F1}$ of the first face 317 of the notch 315 and the longitudinal axis $A_L$ is acute with respect to the first direction GG, the force exerted on the loop 412 of the suture 410 by the first face 317 of the notch 315 retains the loop 412 of the suture 410 in the notch 315 as the delivery device 310 is moved in the first direction GG.

Once the tissue anchor 420 reaches a depth within the tissue where it is to be disposed, the medical practitioner can release the loop 412 of the suture 410 from the notch 315 of the delivery device 310 by moving the delivery device 310 in a second direction along the longitudinal axis AL shown by the arrow HH in FIG. 8. The second direction HH is substantially opposite the first direction GG. Because the angle eF2 defined by the axis $A_{F2}$ of the second face 316 of the notch 315 and the longitudinal axis AL is obtuse with respect to the second direction HH, the loop 412 of the suture 410 is released from the notch 315 as the delivery device 310 is moved in the second direction HH. Said another way, when the delivery device 310 is moved in the second direction HH, the second face 316 of the notch 315 exerts a force on the loop 412 of the suture 410 that is normal to the second face 316. This force pushes the loop 412 of the suture 410 out of the notch 315. Once the loop 412 of the suture 410 is released from the notch 315, the medical practitioner can remove the delivery device 310 from the tissue of the patient by continuing to move the delivery device 310 in the second direction HH.

Figure 9:
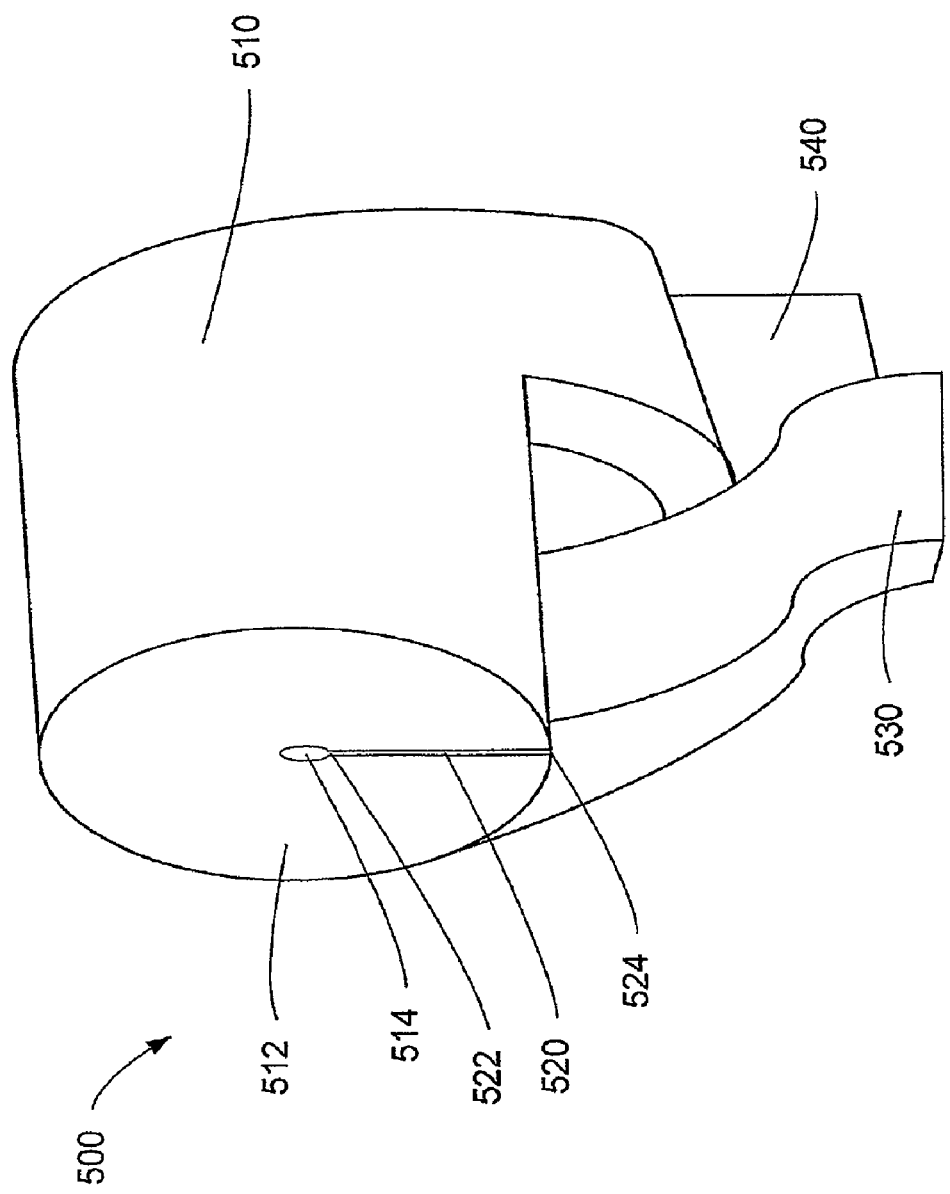
FIG. 9 is a perspective view of an adjustable stop, according to an embodiment.

FIG. 9 is a side perspective view of an adjustable stop 500, according to another embodiment. The adjustable stop 500 is configured to limit the depth the delivery device can be inserted into a tissue of a patient. The adjustable stop 500 includes a body portion 510, a first leg portion 530 and a second leg portion 540. The body portion 510 includes a first face 512 and a second face (not shown). The first face 512 of the body portion 510 are shown in FIG. 9 as being substantially circular in shape. In other embodiments, faces of the body portion can be any other suitable shape, such as, for example, triangular, square, and/or hexagonal.

The body portion 510 defines a lumen 514 and a slit 520. The lumen 514 extends the entire length of the body portion 510 of the adjustable stop 500. Said another way, the lumen extends from the first face 512 of the body portion 510 to the second face (not shown) of the body portion 510.

The first leg portion 530 of the adjustable stop 500 and the second leg portion 540 of the adjustable stop 540 extend from the body portion 510 of the adjustable stop 500. The first leg portion 530 and the second leg 540 portion cross each other as shown in FIG. 9.

Figure 10:
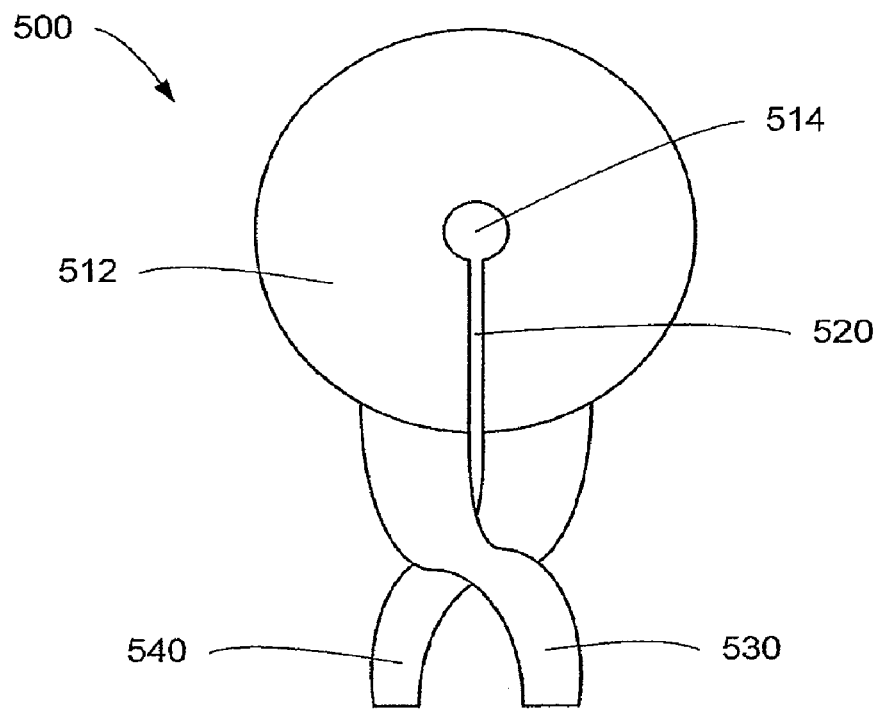
FIGS. 10 and 11 are front views of the adjustable stop of FIG. 9 in a first configuration and a second configuration, respectively.
Figure 11:
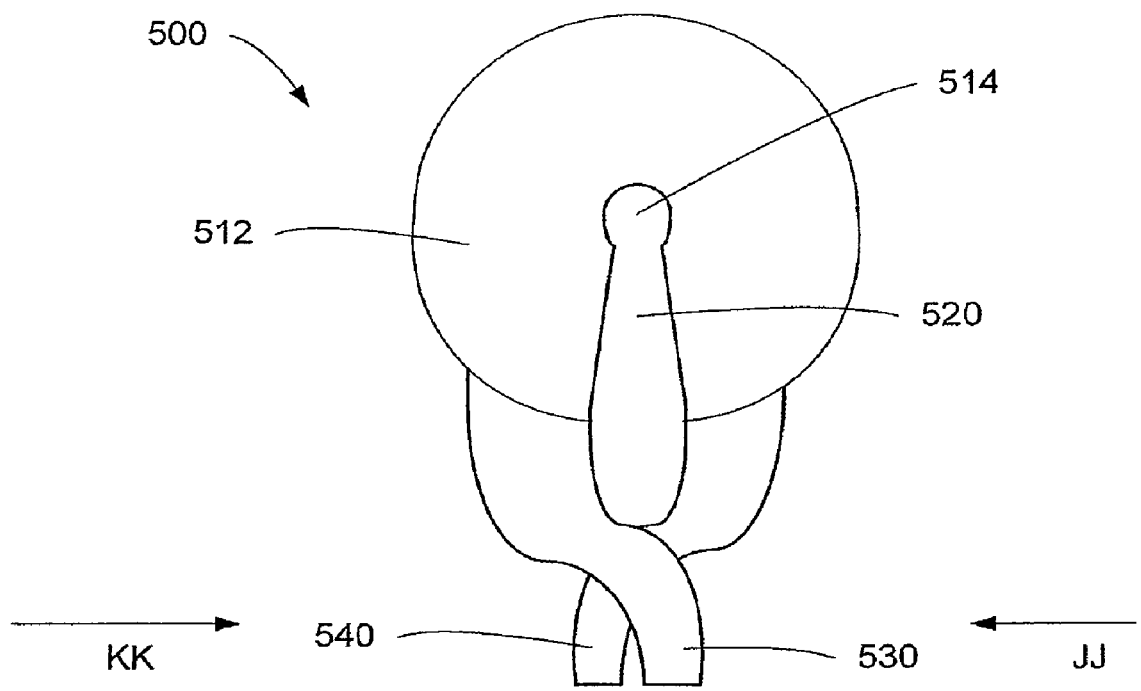

The adjustable stop 500 has a first configuration and a second configuration, as shown in FIG. 10 and FIG. 11 respectively. When the adjustable stop 500 is in its first configuration (FIG. 10), the lumen 514 has a size that is substantially equal to the size of a delivery device, such as the delivery device 310 shown and described in FIG. 5. Additionally, when the adjustable stop 500 is in its first configuration, the slit 520 has a width that is less than a width of the delivery device. As such, a delivery device not disposed within the lumen 514 is prevented from passing through the slit 520 and into the lumen 514 and a delivery device disposed within the lumen 514 (see e.g., FIG. 12) is prevented from passing through the slit 520 to be removed from the lumen 514. Further, the position of the adjustable stop 500 with respect to a delivery device disposed within the lumen 514 is fixed. Thus, the adjustable stop 500 is unable to move with respect to a delivery device disposed within the lumen 514 when the adjustable stop 500 is in its first configuration.

When the adjustable stop 500 is in its second configuration (FIG. 11) the lumen 514 has a size that is greater than the size of the delivery device. As such, the delivery device can be inserted into the lumen 514 and the adjustable stop 500 can move with respect to the delivery device. For example, the adjustable stop 500 can slide along the delivery device in a direction substantially parallel to a longitudinal axis defined by the delivery device.

The width of the slit 520 in the second configuration is greater than the width of the slit 520 in the first configuration. The width of the slit 520 in the second configuration, however, is smaller than the width of the delivery device. As such, similar to the first configuration, the delivery device cannot pass through the slit 520. This prevents the delivery device from inadvertently being removed from the lumen 514 when the adjustable stop 500 is in its second configuration.

The adjustable stop 500 can be moved from its first configuration (FIG. 10) to its second configuration (FIG. 11) by squeezing the first leg portion 530 and the second leg portion 540 together. Specifically, to move the adjustable stop 500 into its second configuration a force in the direction shown by the arrow JJ is exerted on the first leg portion 530 and a force in the direction shown by the arrow KK is exerted on the second leg portion 540. This causes the lumen 514 and the slit 520 to expand. As discussed above, once in the second configuration, the adjustable stop 500 can be coupled to the delivery device and can be moved with respect to the delivery device.

The adjustable stop 500 is biased in its first configuration. Thus, to return the adjustable stop 500 to its first configuration, the force exerted on the first leg portion 530 and the force exerted on the second leg portion 540 are released. This causes the lumen 514 and the slit 520 to contract back to the first configuration.

The adjustable stop 500 is configured to help limit the distance that a distal end portion of the delivery device can be inserted into the tissue of the patient. The distance that the distal end portion of the delivery device can be inserted into the patient is substantially equal to the distance between the distal end portion of the delivery device and the adjustable stop 500. Having an adjustable stop 500 prevents a medical practitioner from inserting the distal end portion of the delivery device into the tissue of the patient further than expected, causing unwanted harm. The adjustable stop 500 also provides the medical practitioner with the ability to determine a depth within the tissue of the patient where a distal end portion of a suture and/or a tissue anchor of the suture is to be disposed, and, using the adjustable stop 500, setting the delivery device to deliver the distal end portion of the suture 500 and/or the tissue anchor of the suture to this depth, as further described in detail herein.

Figure 12:
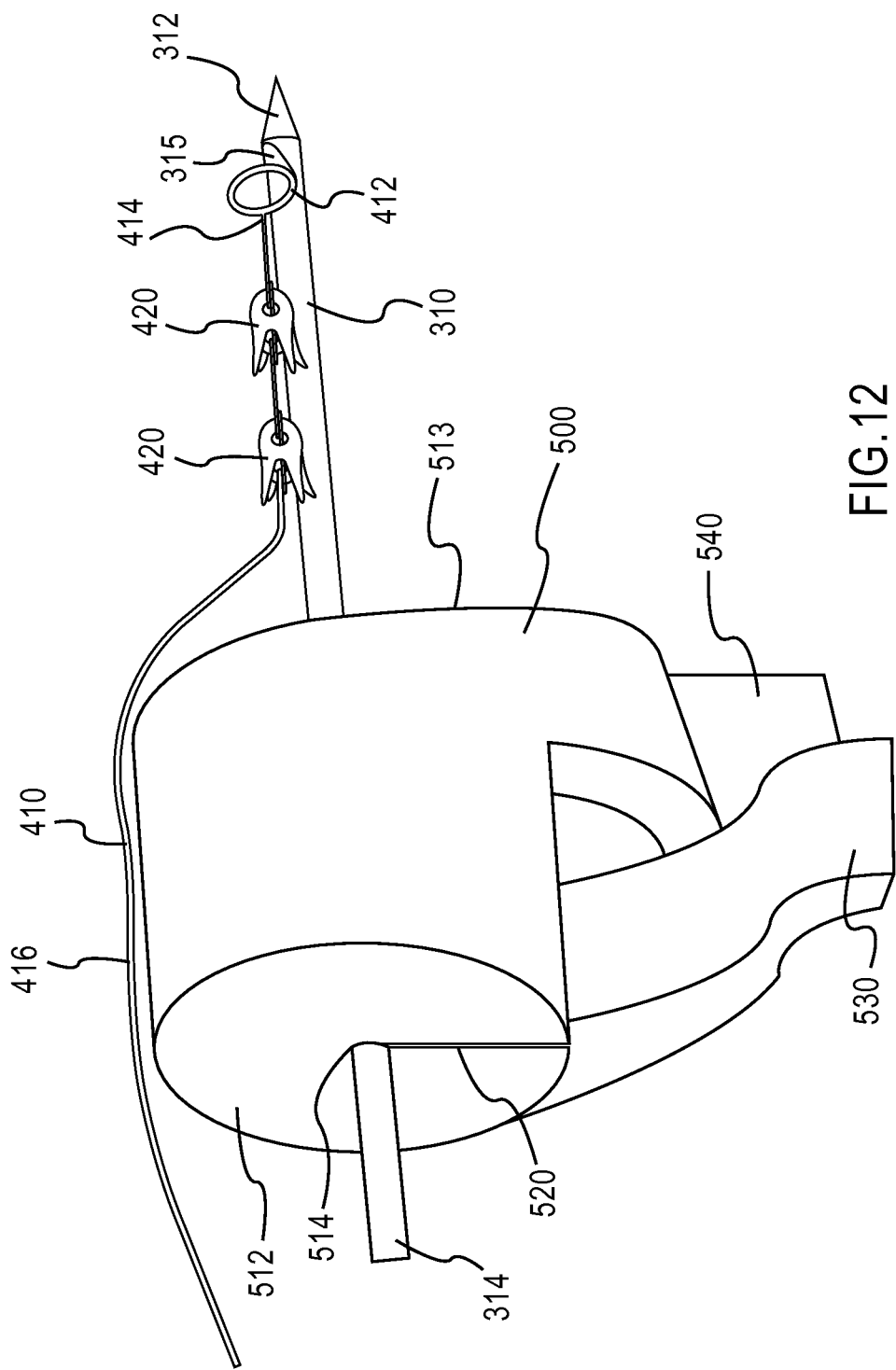
FIG. 12 is a perspective view of the adjustable stop of FIG. 9 and the suture of FIG. 6 coupled to the delivery device of FIG. 5.

In use, the adjustable stop 500 is moved into its second configuration and coupled to the delivery device. FIG. 12 shows the adjustable stop 500 coupled to the delivery device 310 of FIG. 5. The adjustable stop 500 can be moved with respect to the delivery device 310 in order to set a depth to which a distal end portion 414 of a suture 410 or a tissue anchor 420 of the suture 410 will be disposed. Once the adjustable stop 500 is in the desired position with respect to the delivery device 310, it is moved from its second configuration to its first configuration. As described above, when the adjustable stop 500 is in its first configuration, the position of the adjustable stop 500 with respect to the delivery device 310 is substantially fixed.

A suture 410 is releasably coupled to the distal end portion 312 of the delivery device 310. This can be accomplished by any of the methods described above. The distal end portion 312 of the delivery device 310 is inserted into the tissue of the patient in a first direction until the second face (not shown) of the adjustable stop contacts the outer surface of the tissue. Once the second face of the adjustable stop contacts the outer surface of the tissue, the distal end portion 312 of the delivery device 310 cannot be inserted deeper into the tissue (i.e., the skin near the insertion site). The suture is released from the distal end portion of the delivery device and the distal end portion of the delivery device removed from the tissue of the patient by moving the delivery device in a second direction, substantially opposite the first direction.

Figure 13:
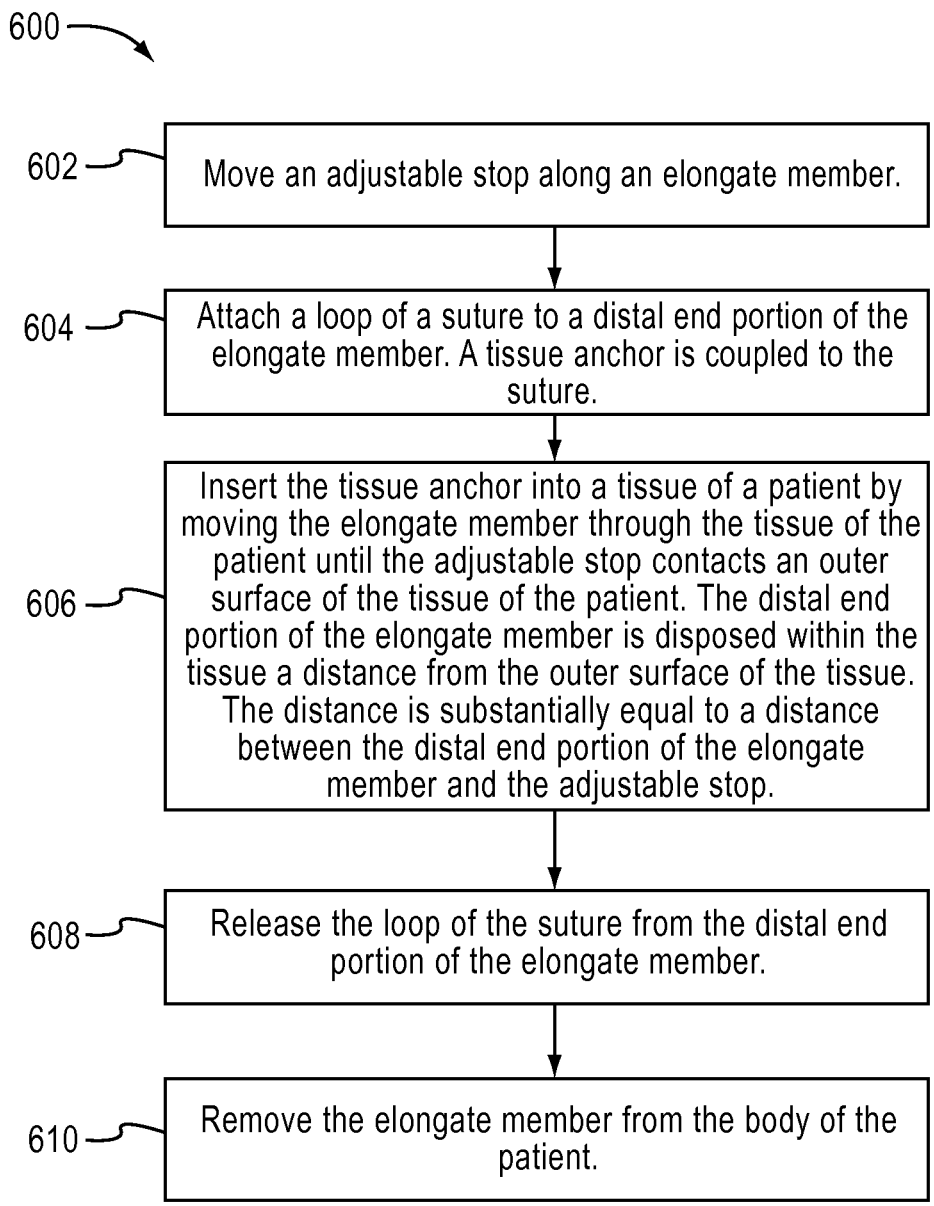
FIG. 13 is a flow chart illustrating a method of placing a suture within a body of a patient according to an embodiment.

FIG. 13 is a flow chart illustrating a method 600 of placing a suture within a body of a patient, according to another embodiment. The method 600 includes moving an adjustable stop along an elongate member, at 602. The elongate member is a portion of a delivery device. In some embodiments, the delivery device is structurally and functionally similar to the delivery devices shown and described herein. In some embodiments, the adjustable stop is structurally and functionally similar to the adjustable stops shown and described herein.

A loop of a suture is attached to a distal end portion of the elongate member, at 604. A tissue anchor is coupled to the suture. The suture can be attached to the distal end portion of the elongate member by any suitable method. In some embodiments, for example, the suture has a loop configured to attach to a notch defined by the elongate member as shown and described herein. In other embodiments, the suture can be attached to the distal end portion of the elongate member using a clip, an adhesive, glue and/or any other attachment mechanism known in the art.

The tissue anchor is inserted into a tissue of a patient by moving the elongate member through the tissue of the patient until the adjustable stop contacts an outer surface of the tissue of the patient, at 606. The distal end portion of the elongate member is disposed within the tissue a distance from the outer surface of the tissue. The distance is substantially equal to a distance between the distal end portion of the elongate member and the adjustable stop.

The loop of the suture is released from the distal end portion of the elongate member. This can be done by any suitable method. In some embodiments, for example, the elongate member is moved in a direction substantially opposite the direction in which the elongate member was moved to insert the tissue anchor, as shown and described herein. In such embodiments, the movement in the opposite direction causes the loop of the suture to release from the distal end portion of the elongate member. In other embodiments, the loop of the suture can be released from the distal end portion of the elongate member by releasing a clip, waiting for an adhesive to dissolve, moving a switch on a handle, and/or the like.

The elongate member is then removed from the body of the patient. This can be done by moving the elongate member in a direction substantially opposite the direction in which the elongate member was moved to insert the tissue anchor.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, while a single type of adjustable stop is described, any adjustable stop capable of limiting the depth a distal end portion of a delivery device can be inserted into a tissue can be used. For example, the adjustable stop might have a different shape, size, and/or method of moving between its first configuration and its second configuration. In some embodiments, for example, the adjustable stop is moved between its first configuration and its second configuration by use of a switch, a dial, a screw, and/or any other mechanism known in the art.

Although various embodiments have been described as having particular features and/or combinations of components, other embodiments are possible having a combination of any features and/or components from any of embodiments where appropriate.

An apparatus includes an elongate member having a distal end portion and a proximal end portion. The elongate member defines a longitudinal axis. The distal end portion of the elongate member defines a notch having a face defining an axis. The axis of the face and the longitudinal axis define an acute angle with respect to a first direction along the longitudinal axis. The notch is configured to retain a loop of a suture when the elongate member is moved through a tissue of a patient in the first direction along the longitudinal axis. The notch is configured to release the loop of the suture when the elongate member is moved through the tissue of the patient in a second direction different than the first direction. The suture has at least one tissue anchor configured to be disposed within the tissue of the patient.

In some embodiments, the loop of the suture remains within the tissue of the patient when the elongate member is moved in the second direction.

In some embodiments, the apparatus further includes an adjustable stop coupled to the elongate member. The adjustable has a first configuration and a second configuration. The adjustable stop is configured to move with respect to the elongate member when in the first configuration and is configured to maintain its position with respect to the elongate member when in the second configuration. The adjustable stop is configured to limit the distance between an outer surface of the tissue and the distal end portion of the elongate member when the adjustable stop is in its second configuration and the elongate member is inserted into the tissue of the patient such that the adjustable stop contacts the outer surface of the tissue.

In some embodiments, the tissue anchor is configured to allow movement of the suture through the tissue of the patient in the first direction and configured to limit movement of the suture through the tissue of the patient in the second direction. In some embodiments, the distal end portion of the elongate member includes a tissue piercing portion configured to penetrate the tissue of the patient.

In some embodiments, the elongate member is substantially solid. In some embodiments, the elongate member is substantially rigid. In some embodiments, the face of the notch is a first face of the notch and the notch has a second face defining an axis. The axis of the second face and the longitudinal axis define an obtuse angle with respect to the second direction.

In some embodiments, a method includes sliding an adjustable stop along an elongate member. A loop of a suture is attached to a distal end portion of the elongate member. A tissue anchor is coupled to the suture. The tissue anchor is inserted into a tissue of a patient by moving the elongate member through the tissue of the patient until the adjustable stop contacts an outer surface of the tissue of the patient. The distal end portion of the elongate member is disposed within the tissue a distance from the outer surface of the tissue. The distance is substantially equal to a distance between the distal end portion of the elongate member and the adjustable stop. The loop of the suture is released from the distal end portion of the elongate member and the elongate member is removed from the body of the patient.

In some embodiments, the inserting includes penetrating the tissue of the patient with the distal end portion of the elongate member. In some embodiments, the inserting includes moving the elongate member through the tissue of the patient in a first direction and the releasing includes moving the elongate member in a second direction substantially opposite the first direction.

In some embodiments, the releasing the loop of the suture from the distal end portion of the elongate member includes moving the elongate member with respect to the tissue of the patient. In some embodiments, the attaching includes inserting the loop of the distal end portion of the suture into a notch defined by the distal end portion of the elongate member.

In some embodiments, the apparatus includes an elongate member having a distal end portion and a proximal end portion and an adjustable stop movably coupled to the elongate member. The distal end portion of the elongate member defines a notch configured to releasably retain a loop of a suture when the elongate member is inserted into a tissue of a patient a distance. The adjustable stop is configured to allow a user to determine the distance the elongate member is inserted into the tissue.

In some embodiments, the adjustable stop defines a face configured to contact an outer portion of the tissue when the elongate member is inserted into the tissue the distance. In some embodiments, the distance is a first distance and the adjustable stop has a first position with respect to the elongate member and a second position with respect to the elongate member. The elongate member is configured to be inserted into the tissue of the patient the first distance when the adjustable stop is in the first position. The elongate member is configured to be inserted into the tissue of the patient a second distance when the adjustable stop is in the second position. The second distance is greater than the first distance.

In some embodiments, the elongate member defines a longitudinal axis and is configured to be inserted into the tissue of the patient in a direction substantially along the longitudinal axis. In some embodiments, the adjustable stop is configured to move with respect to the elongate member. In some embodiments, the notch is configured to retain the loop of the suture when the elongate member is moved in a first direction through the tissue of the patient. The notch is configured to release the loop of the suture when the elongate member is moved in a second direction substantially opposite the first direction.

In some embodiments, the elongate member is substantially solid. In some embodiments, the elongate member is substantially rigid. In some embodiments, at least one tissue anchor configured to be disposed within the tissue of the patient is coupled to the suture.

In some embodiments, an apparatus includes an elongate member having a distal end portion and a proximal end portion. The elongate member defines a longitudinal axis and an outer perimeter. The distal end portion of the elongate member has a tissue piercing tip and an oblique shoulder facing toward the tissue piercing tip. The oblique shoulder is disposed proximal to the tissue piercing tip along the longitudinal axis and is within the outer perimeter defined by the elongate member.

In some embodiments, the oblique shoulder is configured to retain a loop of a suture when the elongate member is moved through a tissue of a patient in the first direction along the longitudinal axis. The oblique shoulder is configured to release the loop of the suture when the elongate member is moved through the tissue of the patient in a second direction different than the first direction. The suture has at least one tissue anchor configured to be disposed within the tissue of the patient.

In some embodiments, the elongate member is substantially solid. In some embodiments, the elongate member is substantially rigid. In some embodiments the apparatus further includes an adjustable stop coupled to the elongate member. The adjustable stop has a first configuration and a second configuration. The adjustable stop is configured to move with respect to the elongate member when in the first configuration and is configured to maintain its position with respect to the elongate member when in the second configuration. The adjustable stop is configured to limit the distance between an outer surface of the tissue and the distal end portion of the elongate member when the adjustable stop is in its second configuration and the elongate member is inserted into the tissue of the patient such that the adjustable stop contacts the outer surface of the tissue.

In some embodiments, a medical device includes an elongate member having a distal end portion and a proximal end portion, a suture having a distal end portion and a proximal end portion and an anchor coupled to the suture. The distal end portion of the elongate member defines a notch. The distal end portion of the suture has a loop configured to be inserted into the notch. The notch is configured to retain the loop of the suture when the elongate member is inserted into a tissue of a patient. The anchor is configured to retain the suture within the tissue of the patient when the suture is disposed within the tissue of the patient and the elongate member is removed from the tissue of the patient.

In some embodiments, the anchor is configured to allow movement of the suture through the tissue of the patient in a first direction and is configured to help prevent movement of the suture through the tissue of the patient in a second direction substantially opposite the first direction.

In some embodiments, the medical device further includes an adjustable stop coupled to the elongate member. The adjustable stop has a first configuration and a second configuration. The adjustable stop is configured to move with respect to the elongate member when in the first configuration. The adjustable stop is configured to maintain its position with respect to the elongate member when in the second configuration. The adjustable stop configured to limit the distance between an outer surface of the tissue and the distal end portion of the elongate member when the adjustable stop is in its second configuration and the elongate member is inserted into the tissue of the patient such that the adjustable stop contacts the outer surface of the tissue.

In some embodiments, the notch of the distal end portion of the elongate member has a face defining an axis. The axis and a longitudinal axis defined by the elongate member define an acute angle with respect to a distal direction.

In some embodiments, the distal end portion of the elongate member includes a tissue piercing portion configured to penetrate the tissue of the patient. In some embodiments, the elongate member is substantially solid. In some embodiments, the elongate member is substantially rigid.

What is claimed is:

1. An apparatus, comprising:
  a suture;
  an elongate member having a distal end portion and a proximal end portion, the elongate member defining a longitudinal axis, the distal end portion of the elongate member defining a notch, the notch having a face defining an axis, the axis of the face and the longitudinal axis defining an acute angle with respect to a first direction along the longitudinal axis, the notch configured to retain a loop of the suture when the elongate member is moved through a tissue of a patient in the first direction along the longitudinal axis, the notch configured to release the loop of the suture when the elongate member is moved through the tissue of the patient in a second direction different than the first direction, the suture being coupled to a plurality of tissue anchors configured to be disposed within the tissue of the patient,
  at least one tissue anchor of the plurality of tissue anchors having a first end portion defining a first point and a second end portion defining a second point, the first end portion being opposite the second end portion, the first end portion and the second end portion defining a longitudinal line, the suture being coupled to the first end portion and the second end portion of the at least one tissue anchor and then extending to a first end portion of an adjacent tissue anchor of the plurality of tissue anchors to be coupled thereto,
  the at least one tissue anchor having a body portion defining at least one retaining member configured to permit movement through the tissue in the first direction and limit movement through the tissue in the second direction,
  the at least one tissue anchor defining a first opening and a second opening, the suture being coupled to the at least one tissue anchor at the first end portion by extending through the first opening and looping around the first end portion and at the second end portion by extending from the first end portion through the second opening and looping around the second end portion.

2. The apparatus of claim 1, wherein the loop of the suture remains within the tissue of the patient when the elongate member is moved in the second direction.

3. The apparatus of claim 1, further comprising:
an adjustable stop coupled to the elongate member, the adjustable stop having a first configuration and a second configuration, the adjustable stop configured to move with respect to the elongate member when in the first configuration, the adjustable stop configured to maintain its position with respect to the elongate member when in the second configuration, the adjustable stop configured to limit the distance between an outer surface of the tissue and the distal end portion of the elongate member when the adjustable stop is in its second configuration and the elongate member is inserted into the tissue of the patient such that the adjustable stop contacts the outer surface of the tissue.

4. The apparatus of claim 1, wherein the distal end portion of the elongate member includes a tissue piercing portion configured to penetrate the tissue of the patient.

5. The apparatus of claim 1, wherein the elongate member is substantially solid.

6. The apparatus of claim 1, wherein the elongate member is substantially rigid.

7. The apparatus of claim 1, wherein the face of the notch is a first face of the notch, the notch having a second face defining an axis, the axis of the second face and the longitudinal axis defining an obtuse angle with respect to the second direction.

8. The apparatus of claim 1, wherein the second end portion includes a coupling portion, the coupling portion includes an inner wall of the second opening such that when the suture is coupled to the second end portion, the suture engages the inner wall of the second opening of the second end portion.

9. An apparatus, comprising:
an elongate member having a distal end portion and a proximal end portion, the distal end portion of the elongate member defining a notch configured to releasably retain a loop of a suture when the elongate member is inserted into a tissue of a patient a distance; and
an adjustable stop movably coupled to the elongate member, the adjustable stop configured to allow a user to determine a distance the elongate member is inserted into the tissue, the adjustable stop including a body portion, a first leg portion extending from the body portion, and a second leg portion extending from the body portion, the body portion defining a lumen that extends an entire length of the body portion, the lumen configured to receive the elongate member, the body portion defining a slit that extends from the lumen to an edge of the body portion, the first leg portion and the second leg portion being adjacent to the slit such that end portions of the first leg portion and the second leg portion are configured to move in a direction toward each other to expand the slit disposed between the first leg portion and the second leg portion when viewed from an end of the adjustable stop, the first leg portion and the second leg portion cross each other at approximately mid-portions of the respective first and second leg portions.

10. The apparatus of claim 9, wherein the body portion defines a first face and a second face opposite to the first face, the first face configured to contact an outer portion of the tissue when the elongate member is inserted into the tissue the distance.

11. The apparatus of claim 9, wherein the distance is a first distance, the adjustable stop having a first position with respect to the elongate member and a second position with respect to the elongate member, the elongate member configured to be inserted into the tissue of the patient the first distance when the adjustable stop is in the first position, the elongate member configured to be inserted into the tissue of the patient a second distance when the adjustable stop is in the second position, the second distance being greater than the first distance.

12. The apparatus of claim 9, wherein the elongate member defines a longitudinal axis, the elongate member being configured to be inserted into the tissue of the patient in a direction substantially along the longitudinal axis.

13. The apparatus of claim 9, wherein the notch is configured to retain the loop of the suture when the elongate member is moved in a first direction through the tissue of the patient, the notch being configured to release the loop of the suture when the elongate member is moved in a second direction substantially opposite the first direction.

14. The apparatus of claim 9, wherein the elongate member is substantially solid.

* * * * *